(12) United States Patent
Taku

(10) Patent No.: US 8,918,932 B2
(45) Date of Patent: Dec. 30, 2014

(54) APPARATUS TO SUPPORT A SUBJECT AND HAVING A RECEIVING PLATE WITHIN AN INSERTION HOLE THROUGH WHICH A PORTION OF THE SUBJECT IS INSERTED

(75) Inventor: Masakazu Taku, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/299,708

(22) Filed: Nov. 18, 2011

(65) Prior Publication Data

US 2012/0131749 A1     May 31, 2012

(30) Foreign Application Priority Data

Nov. 29, 2010   (JP) ................................. 2010-265748

(51) Int. Cl.
| | | |
|---|---|---|
| *A61G 13/02* | (2006.01) | |
| *A61B 8/00* | (2006.01) | |
| *A61B 6/04* | (2006.01) | |
| *A61B 5/00* | (2006.01) | |

(52) U.S. Cl.
CPC ............. *A61B 6/0435* (2013.01); *A61B 8/4209* (2013.01); *A61B 8/4461* (2013.01); *A61B 6/0414* (2013.01); *A61B 8/403* (2013.01); *A61B 5/0095* (2013.01); *A61B 5/0091* (2013.01); *A61B 8/406* (2013.01); *A61B 5/708* (2013.01)
USPC ................................... 5/600; 5/601; 378/209

(58) Field of Classification Search
USPC .......................... 5/600, 601; 378/209, 65, 68; 600/407–154
See application file for complete search history.

(56) References Cited

U.S. PATENT DOCUMENTS

| | | | |
|---|---|---|---|
| 5,078,142 A * | 1/1992 | Siczek et al. ...................... | 5/601 |
| 5,609,152 A | 3/1997 | Pellegrino et al. | |
| 5,803,913 A | 9/1998 | Khalkhali et al. | |
| 2008/0208044 A1 | 8/2008 | Lecoq et al. | |
| 2009/0064413 A1 | 3/2009 | Sliski et al. | |
| 2009/0080604 A1 | 3/2009 | Shores et al. | |

FOREIGN PATENT DOCUMENTS

| | | | |
|---|---|---|---|
| JP | 07-303633 A | 11/1995 | |
| JP | H10-248839 A | 9/1998 | |
| JP | 2002-102215 A | 4/2002 | |
| JP | 2004-344480 A | 12/2004 | |
| JP | 2010-179030 A | 8/2010 | |

* cited by examiner

*Primary Examiner* — Peter M Cuomo
*Assistant Examiner* — Brittany Wilson
(74) *Attorney, Agent, or Firm* — Canon USA Inc. IP Division

(57) ABSTRACT

An apparatus includes a bed configured to support a subject and having an insertion hole through which a subject portion that is part of the subject is inserted; a pair of compression plates configured to hold and compress the subject portion when the subject portion is inserted through the insertion hole; and a unit including therein the pair of compression plates and having an opening through which an operator inserts a hand when the subject portion is inserted through the insertion hole. The unit includes a receiving plate at a position opposite to the opening in an insertion direction of the hand within a range of the insertion hole when viewed from the insertion hole.

6 Claims, 34 Drawing Sheets

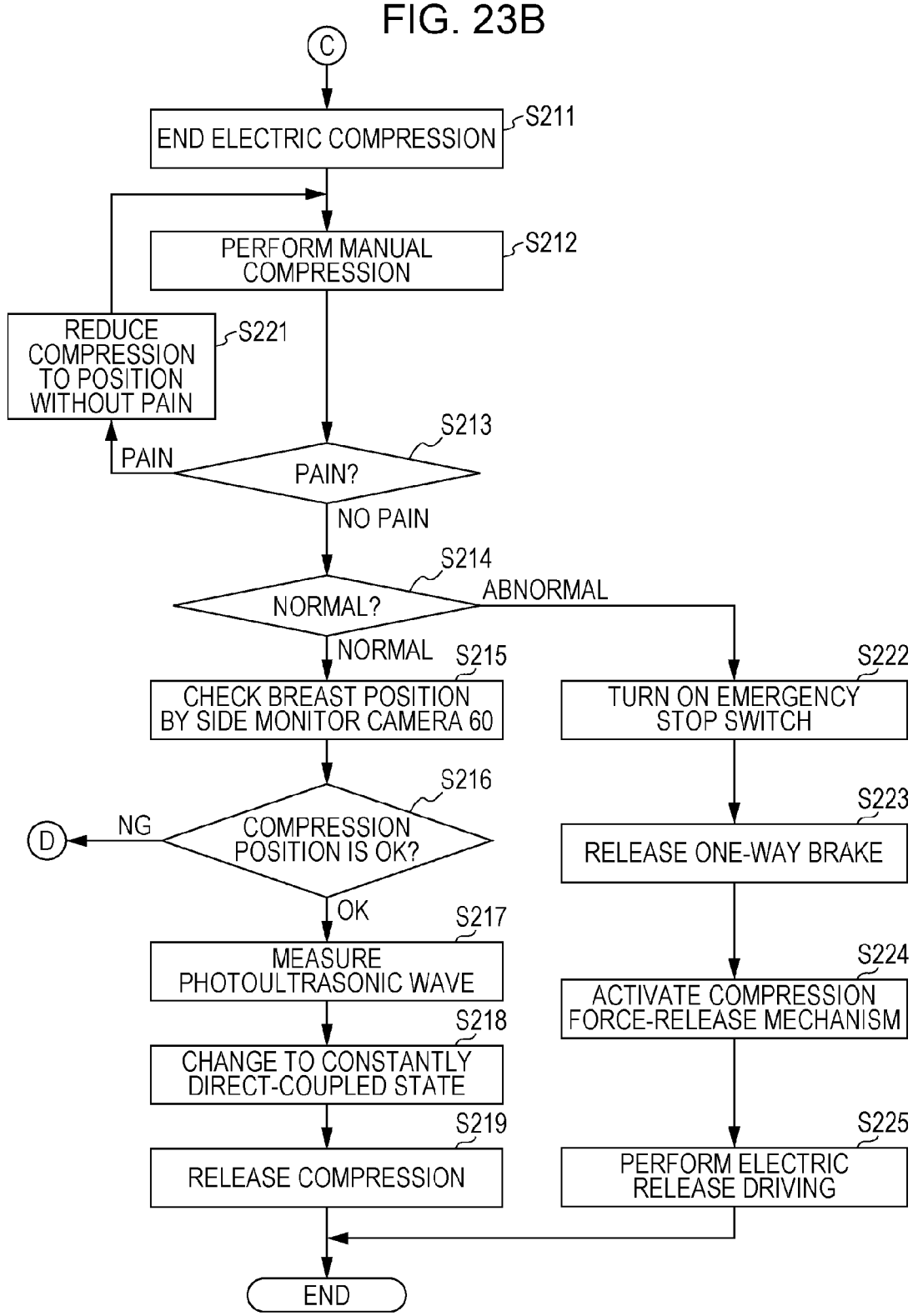

APPARATUS TO SUPPORT A SUBJECT AND HAVING A RECEIVING PLATE WITHIN AN INSERTION HOLE THROUGH WHICH A PORTION OF THE SUBJECT IS INSERTED

BACKGROUND OF THE INVENTION

1. Field of the Invention

The present invention relates to an apparatus.

2. Description of the Related Art

An X-ray diagnostic apparatus or an acoustic-wave acquiring apparatus has been known as an example of a measurement apparatus that acquires biological information. An acoustic-wave acquiring apparatus may be, for example, an apparatus using an ultrasonic echo or an apparatus using a photoacoustic effect. To obtain a good measurement result by such a measurement apparatus, a subject portion has to be non-movably held. If the subject portion is a part of diagnostic interest of a living body, such as a breast, a burdensome discomfort on the subject portion during measurement is desired to be reduced as much as possible to prevent a subject from feeling discomfort.

The photoacoustic effect represents a phenomenon in which when a subject portion is irradiated with pulsed light from a light source such as a laser, the subject portion absorbs optical energy, is expanded and contracted, and generates an acoustic wave (photoacoustic wave). By detecting the photoacoustic wave with use of a probe and performing signal processing and image reconstruction, an optical-property-value distribution in the subject portion is acquired and visualized.

A configuration including a bed that reduces a burdensome discomfort on a subject and a compression unit configured to provide a projected cross-sectional area of a breast sufficient for image-capturing is disclosed in Japanese Patent Laid-Open No. 7-303633 as an example of the X-ray diagnostic apparatus.

FIG. 32 is a schematic illustration showing an X-ray mammography apparatus disclosed in Japanese Patent Laid-Open No. 7-303633. This apparatus includes a bed 113 having a breast insertion hole, a compression plate 102 that compresses a breast 112, and an X-ray film table 101. The X-ray film table 101 is arranged such that the X-ray film table 101 and the compression plate 102 compress the breast 112. The X-ray film table 101 includes therein an X-ray film 105. A subject lies on the bed with her face down during image-capturing and inserts the breast 112 into the breast insertion hole. The inserted breast 112 is inserted to an area between the compression plate 102 and the X-ray film table 101. In this state, the compression plate 102 is moved to compress the breast 112. Then, an X-ray source 117 irradiates the breast 112 with an X-ray beam and an image of the breast 112 is captured.

With the configuration of Japanese Patent Laid-Open No. 7-303633, since the subject lies on the bed with her face down, the breast sags vertically downward. Hence, the projected cross-sectional area becomes large by the sagging amount. However, the bed-type compression mechanism of related art is still desired to be improved to reduce a burdensome discomfort on a subject and to increase ease of operability for an operator.

SUMMARY OF THE INVENTION

According to an aspect of the present invention, an apparatus includes a bed configured to support a subject and having an insertion hole through which a subject portion that is part of the subject is inserted; a pair of compression plates configured to hold and compress the subject portion when the subject portion is inserted through the insertion hole; and a unit including therein the pair of compression plates and having an opening through which an operator inserts a hand when the subject portion is inserted through the insertion hole. The unit includes a receiving plate at a position opposite to the opening in an insertion direction of the hand within a range of the insertion hole when viewed from the insertion hole.

Since the receiving plate is provided, the subject portion can be properly compressed and compression does not have to be unnecessarily repeated. Accordingly, burdensome discomfort on the subject can be reduced, and ease of operability can be increased.

Further features of the present invention will become apparent from the following description of exemplary embodiments with reference to the attached drawings.

BRIEF DESCRIPTION OF THE DRAWINGS

FIGS. 23A and 23B illustrate a flowchart showing a compression sequence according to the embodiment of the present invention.

DESCRIPTION OF THE EMBODIMENTS

According to an embodiment of the present invention, a measurement apparatus includes an apparatus using an ultrasonic echo technique that transmits an ultrasonic wave to a subject portion and receives a reflected wave (reflected ultrasonic wave) reflected in the subject portion; and an apparatus using a photoacoustic effect that irradiates a subject portion with light (electromagnetic wave) and receives an acoustic wave (typically, ultrasonic wave) generated in the subject portion. The present invention can be also applied to an X-ray diagnostic apparatus like the apparatus described in Japanese Patent Laid-Open No. 7-303633. According to the embodiment of the present invention, an acoustic wave is typically an ultrasonic wave, and includes elastic waves called a sonic wave, an acoustic wave, a photoacoustic wave, and a photo-ultrasonic wave. A probe receives an elastic wave that is generated or reflected in a subject portion.

Basic Configuration

Figure 1:
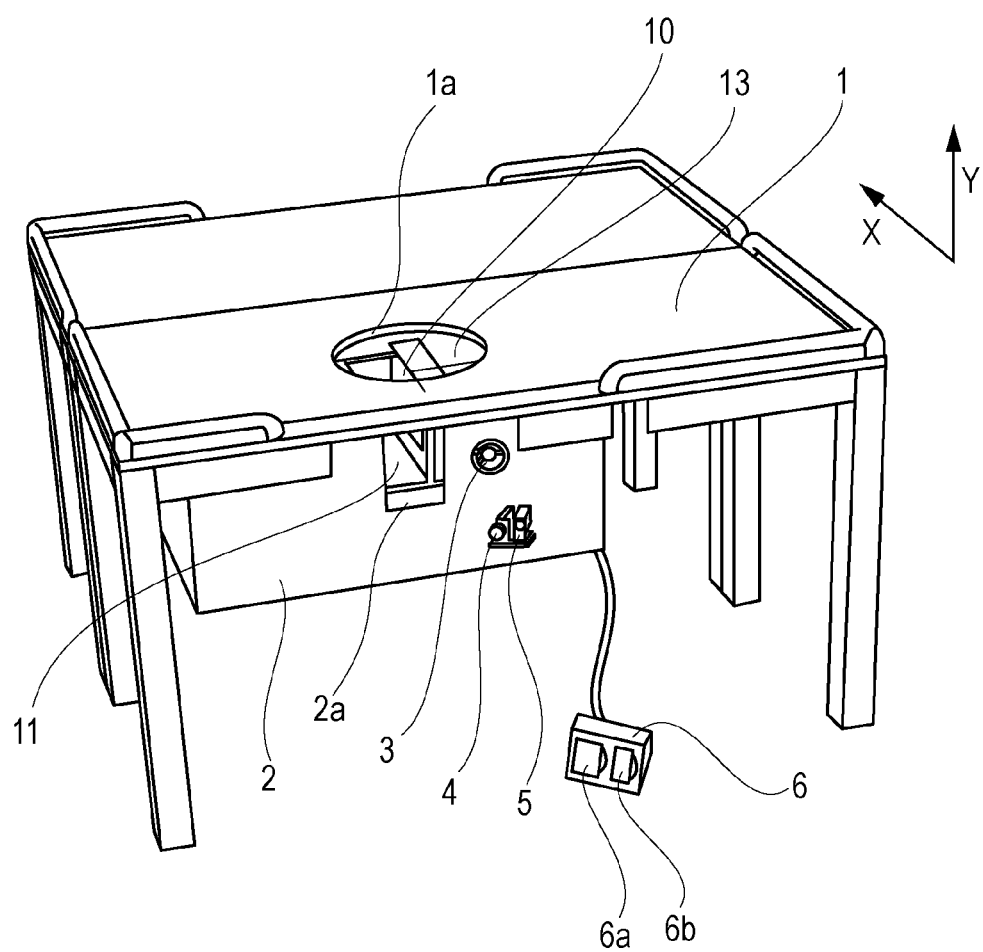
FIG. 1 is an external perspective view showing an acoustic-wave acquiring apparatus to which the present invention can be applied.
Figure 2:
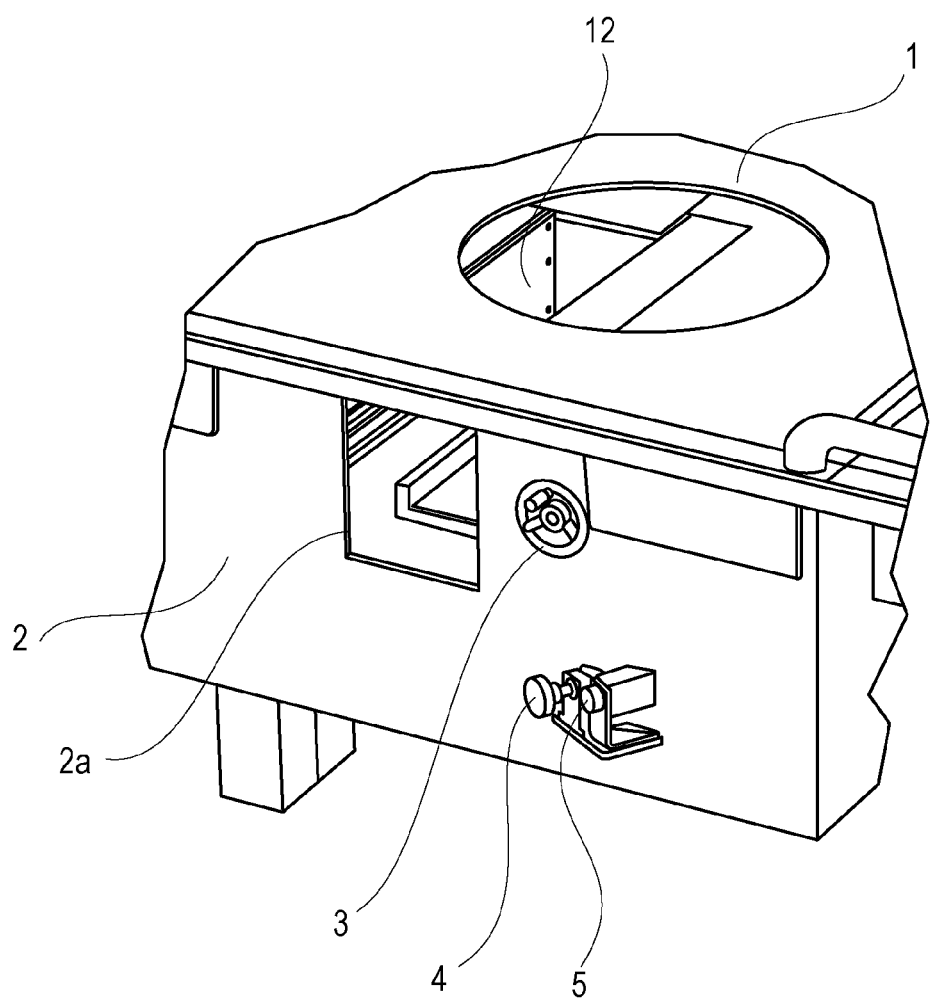
FIG. 2 is a partial perspective view showing the acoustic-wave acquiring apparatus to which the present invention can be applied.

FIGS. 1 and 2 are illustrations showing appearance of an acoustic-wave acquiring apparatus according to an embodiment of the present invention. In the embodiment described here, a breast is measured as a subject portion that is part of the body of a subject. Reference sign 1 denotes a bed that allows a subject to take a prone position (face-down position). Reference sign 2 denotes a compression measurement unit that is hung below a breast insertion hole 1a of the bed 1 in a slidable manner. The compression measurement unit 2 has a manipulation opening 2a for a manipulation when a breast is held and compressed.

By rotating a slide handle 3, the compression measurement unit 2 can slide relative to the bed 1 in a left-right direction. Reference sign 4 denotes a manual compression handle. By rotating the manual compression handle 4, a movable compression plate 12 is advanced toward and retracted from a fixed compression plate 10. The fixed compression plate 10 and the movable compression plate 12 function as a pair of compression plates configured to compress a breast from both sides. Reference sign 5 denotes a state change switch that changes rotation of the manual compression handle 4 between a one-way latch state and a constantly direct-coupled state. The one-way latch state is a state in which the manual compression handle 4 is rotatable when the manual compression handle 4 is rotated in a direction in which the movable compression plate 12 compresses a subject portion (hereinafter, occasionally referred to as compression direction), and the manual compression handle 4 is locked and non-rotatable when the manual compression handle 4 is rotated in a direction in which the movable compression plate 12 releases a subject portion (hereinafter, occasionally referred to as release direction). As described above, since the rotation of the manual compression handle 4 is locked when the manual compression handle 4 is rotated in the release direction of the movable compression plate 12, a reactive force when the movable compression plate 12 compresses a breast is not generated on the manual compression handle 4. An operator does not have to always grip the manual compression handle 4 during compression, and an operation becomes easy.

The constantly direct-coupled state can be set by releasing a one-way mechanism of the one-way latch. The constantly direct-coupled state is a state in which the manual compression handle 4 can be rotated in both the compression direction and the release direction of the movable compression plate 12. This state is used when compression of a subject in a compressed state is released. Reference sign 6 denotes a foot pedal. The foot pedal 6 is a switch that electrically drives the movable compression plate 12 in the compression direction or the release direction, similarly to the operation of the manual compression handle 4.

The foot pedal 6 includes a pedal 6a for driving in the release direction and a pedal 6b for driving in the compression direction. The foot pedal 6 assists the operation of the manual compression handle 4. Reference sign 10 denotes the above-mentioned fixed compression plate that is fixed to the compression measurement unit 2. The fixed compression plate 10 together with the compression measurement unit 2 slides relative to the bed 1 by an operation of the slide handle 3. Accordingly, one-side compression is performed on a breast inserted through the breast insertion hole 1a and an inserted state of the breast can be adjusted by a manipulation.

Reference sign 11 denotes an under tray that is made of a transparent material according to the embodiment of the present invention. A monitor camera (described later) that allows a compression angle of a breast to be checked, and an LED illumination device (described later) that provides optimal illumination to allow the operator to check a compressed state of the breast are installed below the under tray 11.

Reference sign 12 denotes the movable compression plate that is supported by a linear guide (described later), moves in parallel to the fixed compression plate 10, and hence performs compression and release. Reference sign 13 denotes a base plate of the compression measurement unit 2. The base plate 13 slides relative to the bed 1 in a direction perpendicular to a surface of the fixed compression plate 10, which will be described later. Thus, the fixed compression plate 10 can move relative to the bed 1. By bringing a bottom portion (breast portion at the foot side) of the breast into contact with the fixed compression plate 10 and then moving the movable compression plate relative to the fixed compression plate, the inserted state of the breast can be adjusted, and the compressed state of the breast can become proper. Also, the size of the apparatus can be reduced, and the design of the apparatus can attain energy-saving. Further, the compressed state of the breast can be adjusted in the process of manipulation. Hence, the subject does not have to insert the breast again due to an insufficient compressed state.

Measurement Method

FIGS. 3 to 8 are explanatory illustrations of a measurement method for a subject of the apparatus according to the embodiment of the present invention.

Figure 3:
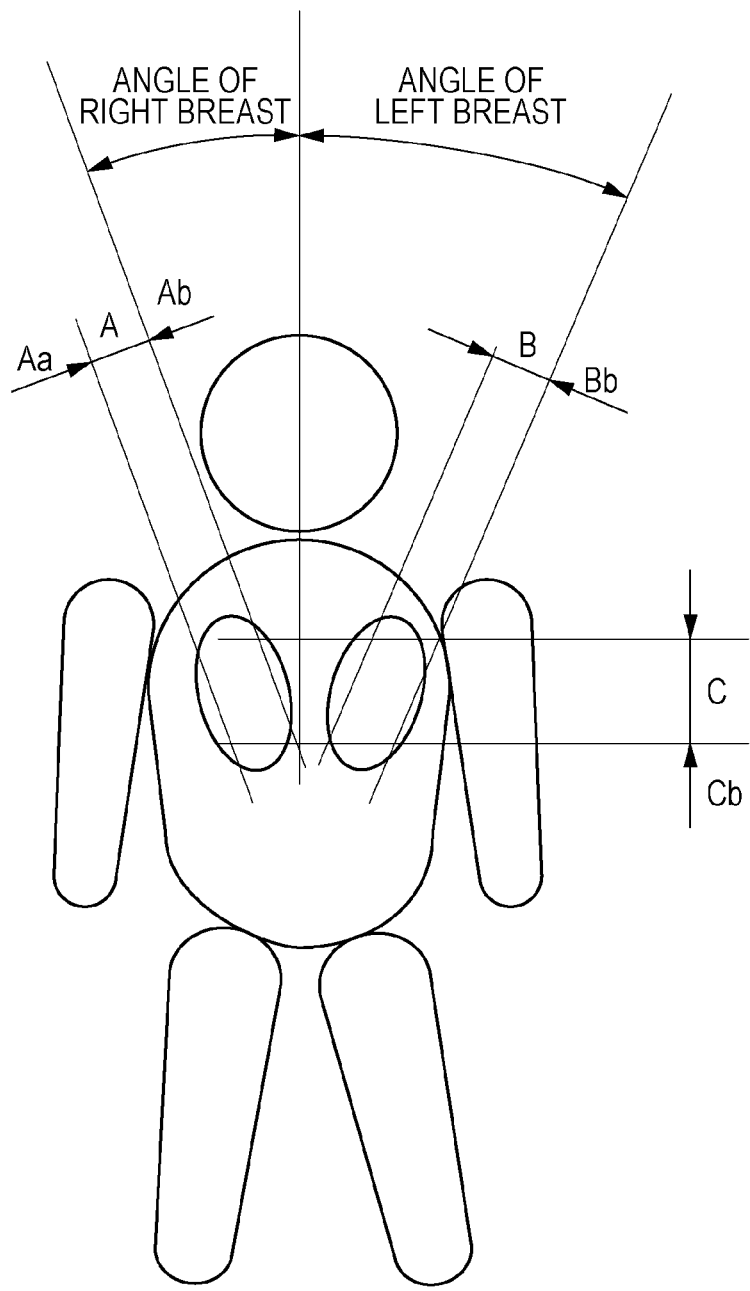
FIG. 3 is an illustration explaining a measurement method.

FIG. 3 is a schematic illustration of a human body. Reference sign A denotes compression in a right medio-lateral oblique (MLO) direction. Reference sign B denotes compression in a left MLO direction. In the embodiment of the present invention, the MLO direction (medio-lateral oblique projection) indicates a medio-lateral oblique direction in which a breast is obliquely compressed. Reference sign C denotes a CC direction in which a breast is compressed from a head side to a foot side. In the embodiment of the present invention, the CC direction (cranio-caudal projection) indicates a cranio-caudal direction. Normally during the compression in the CC direction of reference sign C, a left breast and a right breast are measured individually.

In an X-ray mammography, setting positions of the fixed compression plate 10 and the movable compression plate 12 are determined in the respective compression directions in FIG. 3. A fixed-compression-plate side of each of the A and B positions in the MLO directions in FIG. 3 is an armpit side. In particular, the fixed-compression-plate side of the A position is determined as Aa, and the fixed-compression-plate side of the B position is determined as Bb.

Figure 4:
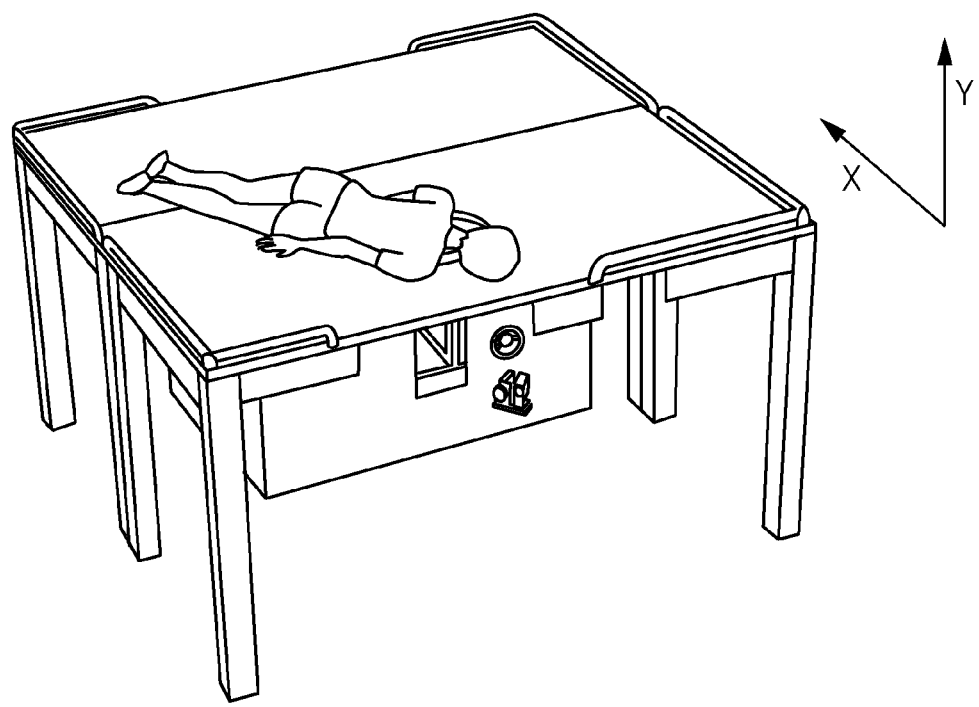
FIG. 4 is an illustration explaining a state during measurement.
Figure 8:
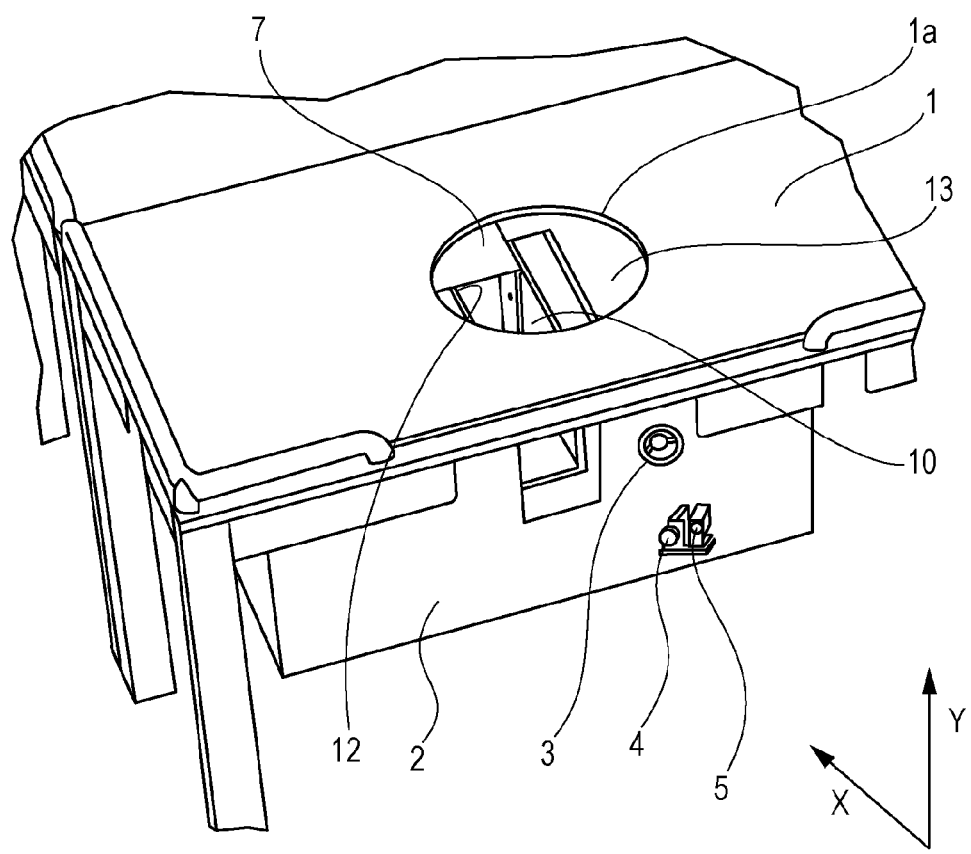
FIG. 8 is a partial perspective view showing the acoustic-wave acquiring apparatus to which the present invention can be applied.

In the embodiment of the present invention, the fixed compression plate 10 is located at Bb that is the same position as the fixed-compression-plate position in an X-ray mammograph during compression at the B position in the MLO direction in FIG. 3. In contrast, during compression at the A position in the MLO direction, as shown in FIG. 4, the fixed compression plate 10 at the A position is set to be located at Ab. This is because, in the embodiment of the present invention, the fixed compression plate 10 is located constantly at the right side of the operator with respect to the manipulation opening 2a. When the fixed compression plate 10 is set at Aa during compression at the A position in the MLO direction similarly to the X-ray mammography, in the case of the bed-type measurement apparatus according to the embodiment of the present invention, a subject may overly on the operator, and hence measurement cannot be carried out. Owing to this, according to the embodiment of the present invention, measurement is performed in the state shown in FIG. 4 such that the fixed compression plate 10 at the A position is located at Ab. Also, according to the embodiment of the present invention, a MLO receiving plate 7 is provided in the compression measurement unit as shown in FIG. 8.

Figure 7:
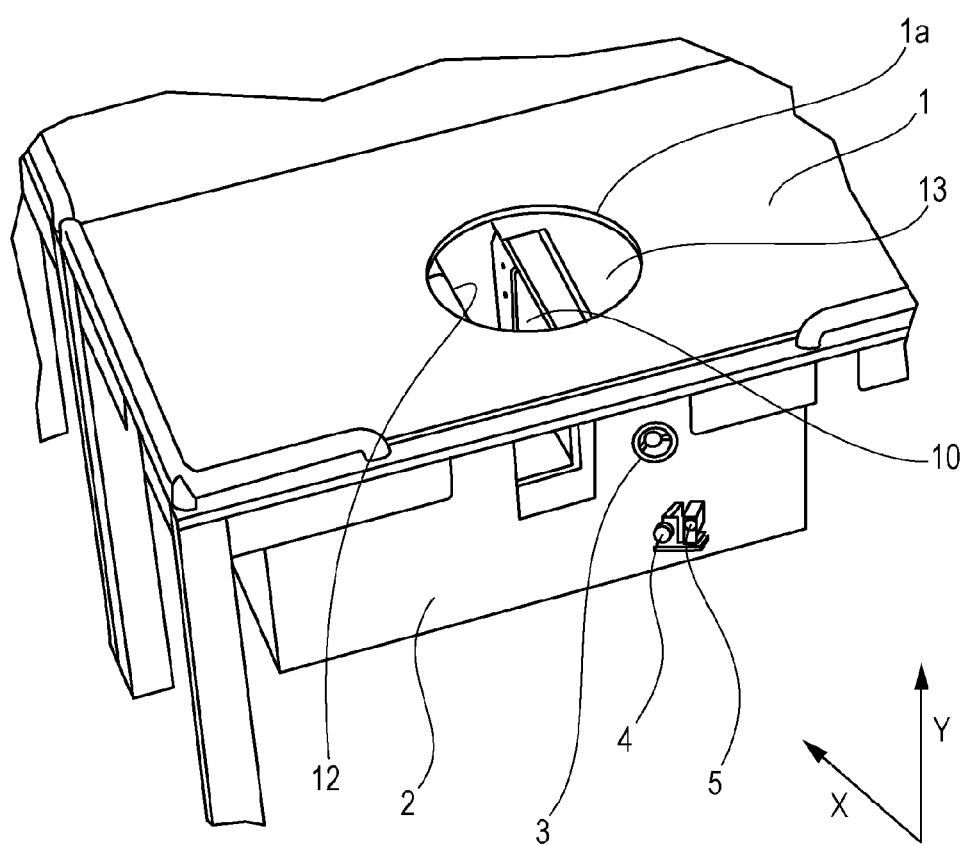
FIG. 7 is a partial perspective view showing the acoustic-wave acquiring apparatus to which the present invention can be applied.

FIG. 7 is a partial perspective view of the measurement apparatus in a state in which the MLO receiving plate 7 is not provided. When the subject takes the prone position in this state for right MLO measurement in FIG. 4, a large gap is present between the fixed compression plate 10 and the movable compression plate 12. Hence, the abdominal portion or the costal portion (part of the body other than the subject portion) of the subject cannot be received by the bed and may protrude to the gap between the compression plates. In this state, when the movable compression plate 12 moves toward the fixed compression plate 10 for compression of the breast, the protruding abdominal portion or costal portion may be compressed before the breast is compressed, and the breast, which is a target of compression, may not be compressed. The size of the breast insertion hole 1a may be decreased so that the abdominal portion or the costal portion does not protrude. In this case, since the bed 1 receives the abdominal portion or the costal portion, it may be difficult to insert the breast to a deep position. Hence, in the embodiment of the present invention, as shown in FIG. 8, the MLO receiving plate 7 is provided below the position of the breast insertion hole 1a (i.e., at a position near the compression plates) in an insertion direction of the breast within a range of the breast insertion hole 1a when viewed from the breast insertion hole. The MLO receiving plate 7 may be located at the same height as the height of upper surfaces of the compression plates in the insertion direction of the breast. The same height as the height of the upper surfaces of the compression plates includes exactly the same height and a position at substantially the same height within a range of assembly accuracy. Also, the MLO receiving plate 7 may have a surface perpendicular to a surface of the fixed compression plate 10.

Alternatively, the MLO receiving plate 7 may be integrally formed with the base plate 13, so that the abdominal portion or the costal portion of the subject is received by the integrated configuration and the abdominal portion of the subject can be prevented from protruding to the gap between the compression plates 10 and 12. Still alternatively, the MLO receiving plate 7 may be made of a flexible material. When the movable compression plate 12 compresses the breast of the subject, although the abdominal portion of the subject slightly protrudes into the gap between the compression plates 10 and 12, the abdominal portion of the subject can slide on an upper surface of the movable compression plate 12. If the receiving plate 7 is made of a flexible material, the material may have Young's modulus in a range from 1.00 to 5.00 GPa. The specific material may be polycarbonate, polyacetal, ABS, or the like.

As described above, according to the embodiment of the present invention, the MLO receiving plate 7 is provided between the compression plates, at a position opposite to the manipulation opening 2a. Accordingly, compression in the CC direction and compression in the MLO direction can be carried out. Also, when compression is performed for medio-lateral direction (medio-lateral projection, ML direction) the direction which is rotated with respect to the CC direction by 90 degrees, the receiving plate 7 allows the breast to be compressed without the abdominal portion or the costal portion of the subject from protruding. Thus, a measurement range can be markedly expanded. Also, different configurations do not have to be provided for CC and MLO. The space and energy of the apparatus can be saved.

Figure 5:
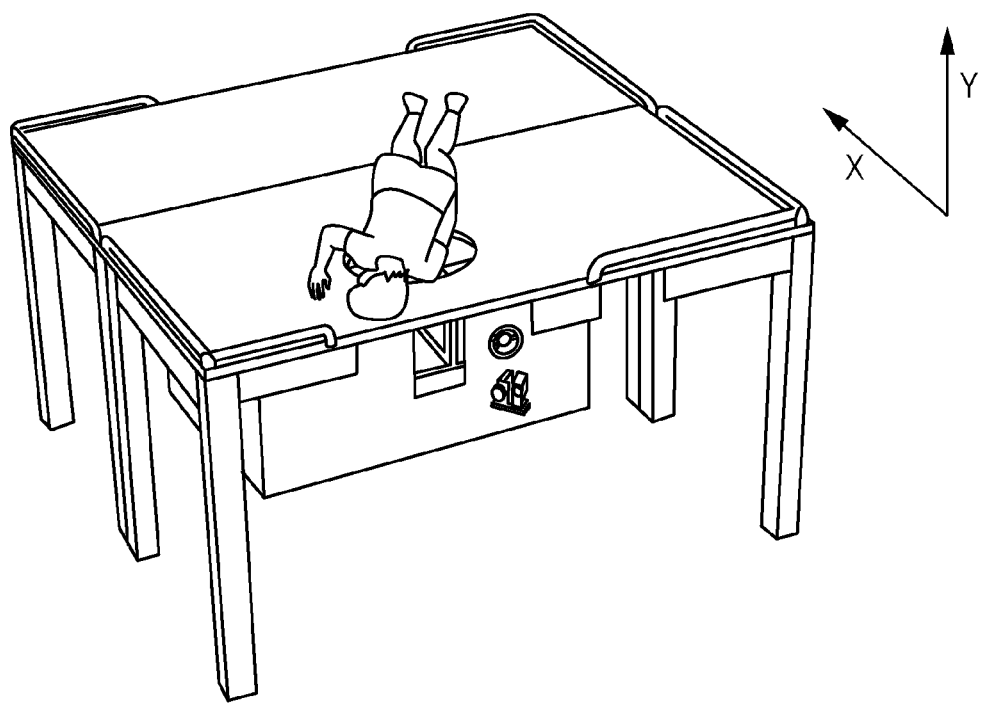
FIG. 5 is an illustration explaining a state during measurement.
Figure 6:
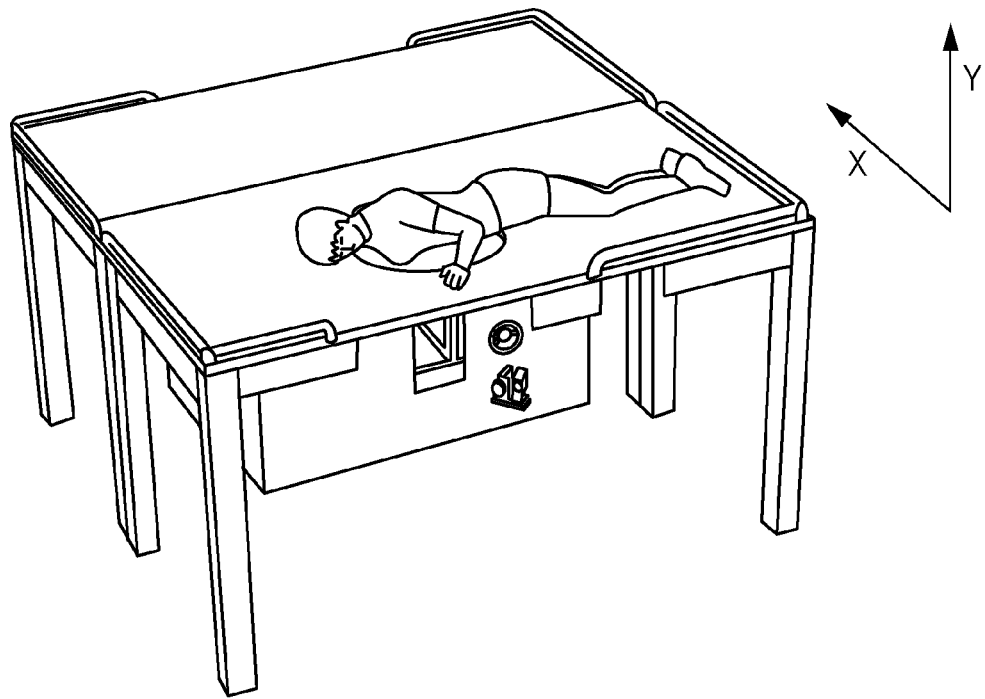
FIG. 6 is an illustration explaining a state during measurement.

FIGS. 4 to 6 are illustrations showing positions of a subject during inspections on the acoustic-wave acquiring apparatus according to the embodiment of the present invention. FIG. 4 illustrates an inspection of a right breast at the A position in FIG. 3 through compression in the MLO direction. FIG. 5 illustrates an inspection of a left breast at the B position in FIG. 3 through compression in the MLO direction. FIG. 6 illustrates an inspection of a right breast at the C position in FIG. 3 through compression in the CC direction.

Operation of Acoustic-wave Acquiring Apparatus

Figure 9:
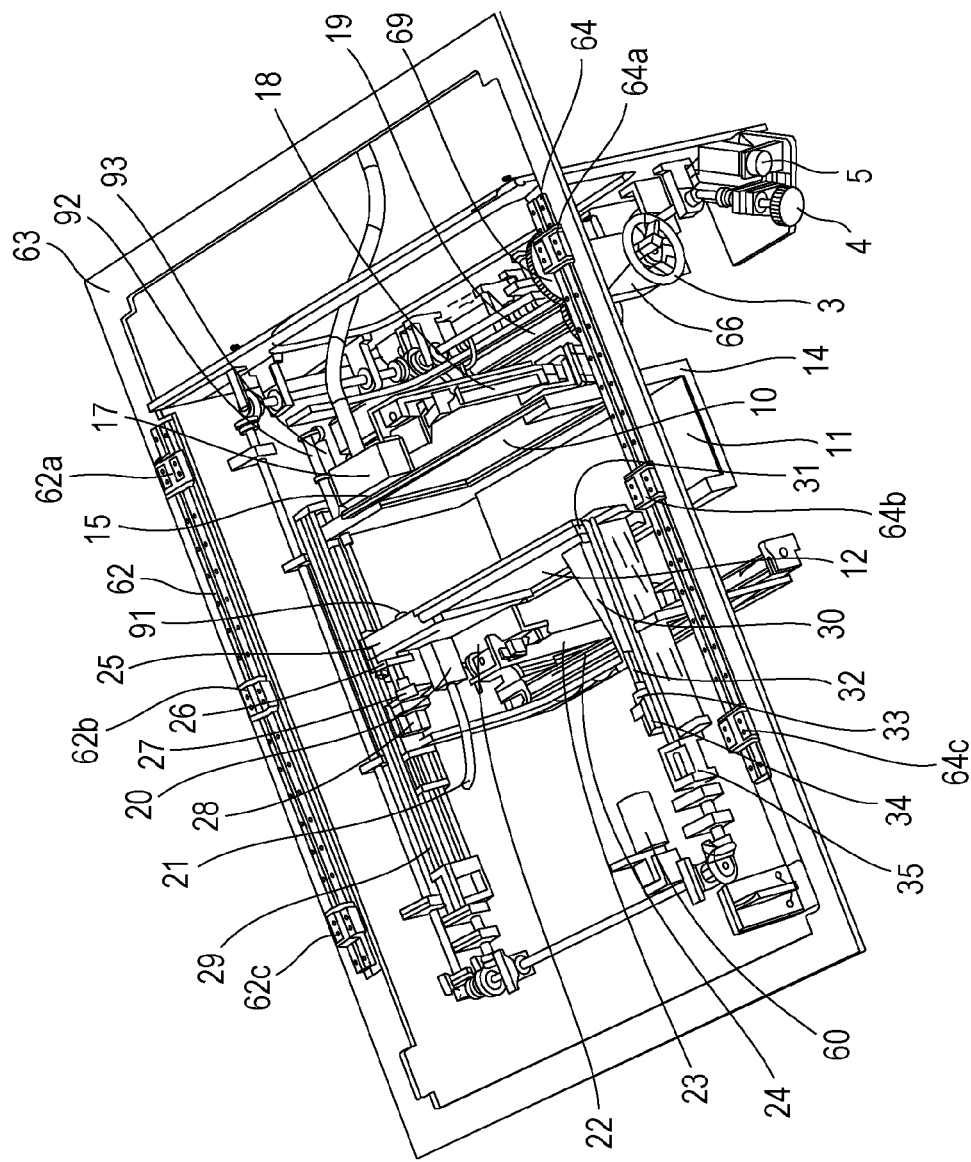
FIG. 9 is a perspective view of a compression mechanism.
Figure 10:
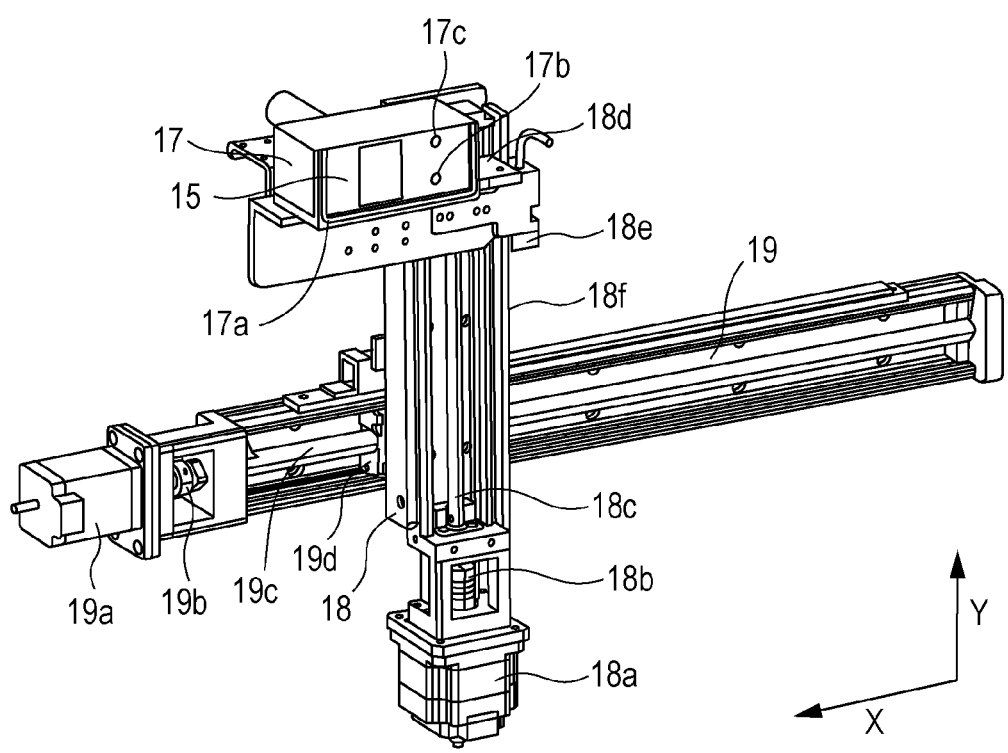
FIG. 10 is a perspective view of a scanning system.
Figure 11:
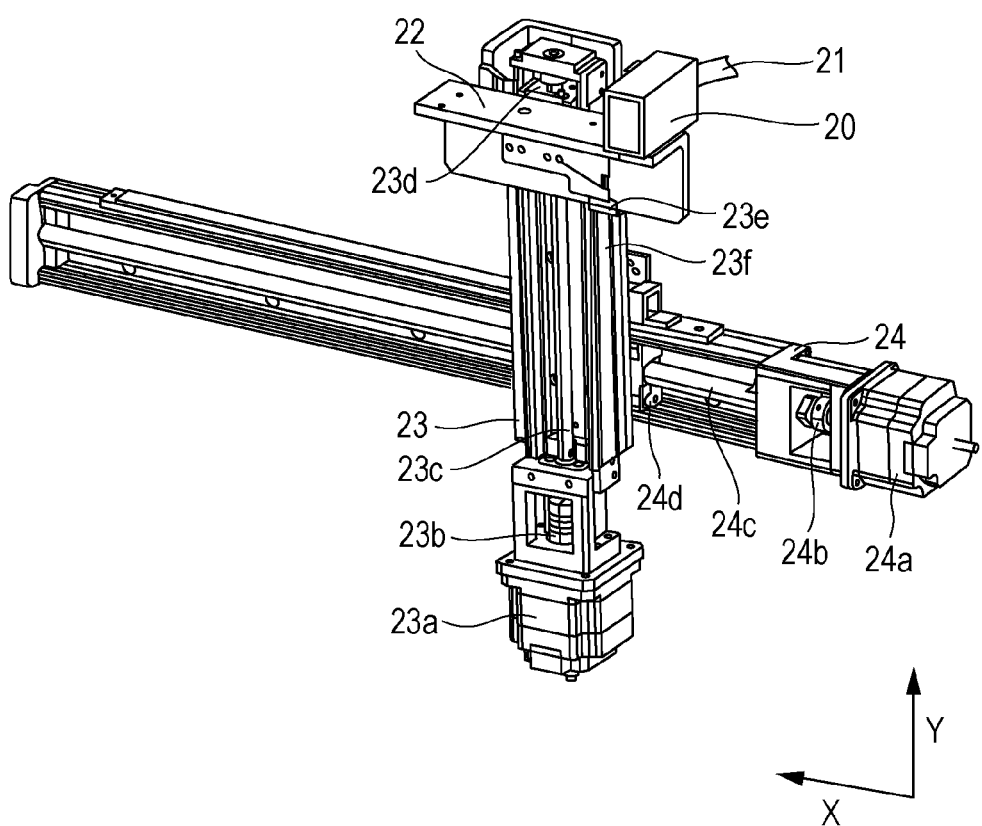
FIG. 11 is a perspective view of the scanning system.

FIGS. 9 to 11 are explanatory perspective views in a state in which the bed 1, the base plate 13, etc., are omitted so that compression and a scanning mechanism are exposed. FIG. 9 is a perspective view showing the entire compression measurement unit 2. An operation of the acoustic-wave acquiring apparatus is described with reference to FIG. 9.

A laser illumination optical system 20 expands and diffuses a pulsed laser beam that is transmitted from a pulsed laser device (not shown) through a fiber cable 21 into a desired size, and illuminates a breast of a subject compressed by the movable compression plate 12 with the pulsed laser beam through the movable compression plate 12.

If a cancer is generated in the breast of the subject, many newborn blood vessels are formed in the cancer, and the amount of blood to the cancer is increased. Blood containing hemoglobin constantly flows in the blood vessels. Hence, if the laser illumination optical system 20 illuminates the breast with the pulsed laser beam (in particular, a near-infrared pulsed laser beam with a wavelength in a range from about 750 to about 1064 nm), the laser beam enters an internal tissue from the surface of the breast while the laser beam is diffused, and the laser beam is absorbed by specific hemoglobin in the blood. The hemoglobin is instantly expanded and contracted. It is known that the instant expansion and contraction of the hemoglobin generates an ultrasonic wave.

The ultrasonic wave propagates to the fixed compression plate 10 through the tissue of the breast, and is received by an ultrasonic probe 15 arranged on a side of the fixed compression plate 10 opposite to the breast. An ultrasonic-wave generation source is re-constructed by processing a signal received by the ultrasonic probe 15 through arithmetic processing similar to that of a typical ultrasonic diagnostic apparatus. Then, the position of a cluster of the specific hemoglobin in the breast of the subject can be determined.

Being able to make a diagnosis on a high probability that a cancer is generated in the cluster portion of the specific hemoglobin is the operating principle of the acoustic-wave acquiring apparatus. If the desired pulsed laser beam illuminates the breast of the subject, the ultrasonic wave is generated from the specific hemoglobin. Hence, a strong ultrasonic wave is generated from a portion where hemoglobin is gathered like a cancer. By specifying the location of generation of the strong ultrasonic wave, the presence of a cancer in the breast and the size of the cancer are determined.

Regarding the operating principle of the acoustic-wave acquiring apparatus, since the pulsed laser beam is diffused in a human body when the pulsed laser beam illuminates the breast, the thickness of the breast has to be reduced as much as possible. Owing to this, the breast is compressed. Also, since the breast is compressed by the movable compression plate 12 and then is illuminated by the laser illumination optical system 20, the material of the movable compression plate 12 has to have a high transmittance for near-infrared radiation. For example, the material may be acrylic resin. Further, the fixed compression plate 10 has to cause the ultrasonic wave generated from the hemoglobin to propagate to the ultrasonic probe 15 through the tissue in the breast.

First, to improve acoustic matching between the breast and the fixed compression plate 10, for example, gel or a urethane gel sheet that is used for ultrasonic diagnosis has to be interposed between the breast and the fixed compression plate 10.

Further, a countermeasure for matching acoustic impedances to improve propagation of the ultrasonic wave has to be provided in the fixed compression plate 10 and in a space from the surface of the fixed compression plate 10 to the ultrasonic probe 15. In the embodiment of the present invention, polymethyl pentene or the like is selected as a material of a countermeasure for a loss of propagation of the ultrasonic wave in the fixed compression plate 10. Also, the space from the surface of the fixed compression plate 10 to the ultrasonic probe 15 is filled with diisodecyl sebacate or called DIDS (coaster oil), PEG (polyethylene glycol), or the like.

FIG. 10 illustrates a filling unit configured to fill the space with DIDS (coaster oil), PEG (polyethylene glycol), or the like. The ultrasonic probe 15 is set such that liquid does not leak to a carriage 17. A packing 17a is mounted on the carriage 17. The packing 17a is pressed to the fixed compression plate 10, and hence a U-shaped space is formed. DIDS (coaster oil), PEG (polyethylene glycol), or the like, is supplied from a supply port 17b by an oil pump (not shown), and discharged from a discharge port 17c.

If the number of ultrasonic sensors in the ultrasonic probe 15 is increased, the ultrasonic probe 15 becomes very expensive. As the result, the area of the ultrasonic probe 15 may become small with respect to the compressed breast. Owing to this, X-Y drive mechanisms as shown in FIGS. 10 and 11 support the ultrasonic probe 15 and the laser illumination optical system 20 for scanning along a plane parallel to the compression plates and acquiring an ultrasonic wave. If the ultrasonic probe 15 and the laser illumination optical system 20 constantly face each other during scanning, the ultrasonic wave can be most efficiently acquired. Owing to this, a probe Y-axis drive guide 18, a probe X-axis drive guide 19, a phototransmitter Y-axis drive guide 23, and a phototransmitter X-axis drive guide 24 are used.

Scanning System

FIGS. 10 and 11 are perspective views showing scanning systems according to the embodiment of the present invention. FIG. 10 shows a scanning system of the ultrasonic probe 15 according to the embodiment of the present invention. The probe Y-axis drive guide 18 includes a drive motor 18a that serves as a power source. The drive motor 18a transmits rotation to a lead screw 18c through a joint 18b and hence drives a linear guide 18d vertically along the Y-axis. The carriage 17 is fixed to the linear guide 18d. When the ultrasonic probe 15 vertically moves along the linear guide 18d, a linear sensor 18e provided on a side surface of the linear guide 18d reads a position at a linear scale 18f and detects a correct scanning position.

The probe X-axis drive guide 19 has a configuration substantially similar to the probe Y-axis drive guide 18. A drive motor 19a is coupled with a lead screw 19c through a joint 19b. The lead screw 19c is rotated and hence a linear guide 19d scans horizontally. The probe Y-axis drive guide 18 is directly mounted on the linear guide 19d, so that the drive mechanism of the probe Y-axis drive guide 18 and the ultrasonic probe 15 scan in the X-axis direction.

FIG. 11 is a perspective view showing the details of the phototransmitter Y-axis drive guide 23 and the phototransmitter X-axis drive guide 24. To perform a facing operation precisely with the probe portion, the phototransmitter portion has a configuration similar to the probe portion. The phototransmitter Y-axis drive guide 23 includes a drive motor 23a that serves as a power source. The drive motor 23a transmits rotation to a lead screw 23c through a joint 23b and hence drives a linear guide 23d vertically along the Y-axis. A phototransmitter carriage 22 is fixed to the linear guide 23d. When the phototransmitter carriage 22 vertically moves along the linear guide 23d, a linear sensor 23e provided on a side surface of the linear guide 23d reads a position at a linear scale 23f and detects a correct scanning position.

The phototransmitter X-axis drive guide 24 has a configuration substantially similar to the phototransmitter Y-axis drive guide 23. A drive motor 24a is coupled with a lead screw 24c through a joint 24b. The lead screw 24c is rotated and hence a linear guide 24d scans horizontally. The phototransmitter Y-axis drive guide 23 is directly mounted on the linear guide 24d, so that the drive mechanism of the phototransmitter Y-axis drive guide 23 and the laser illumination optical system 20 scan in the X-axis direction.

Compression Mechanism

Figure 12:
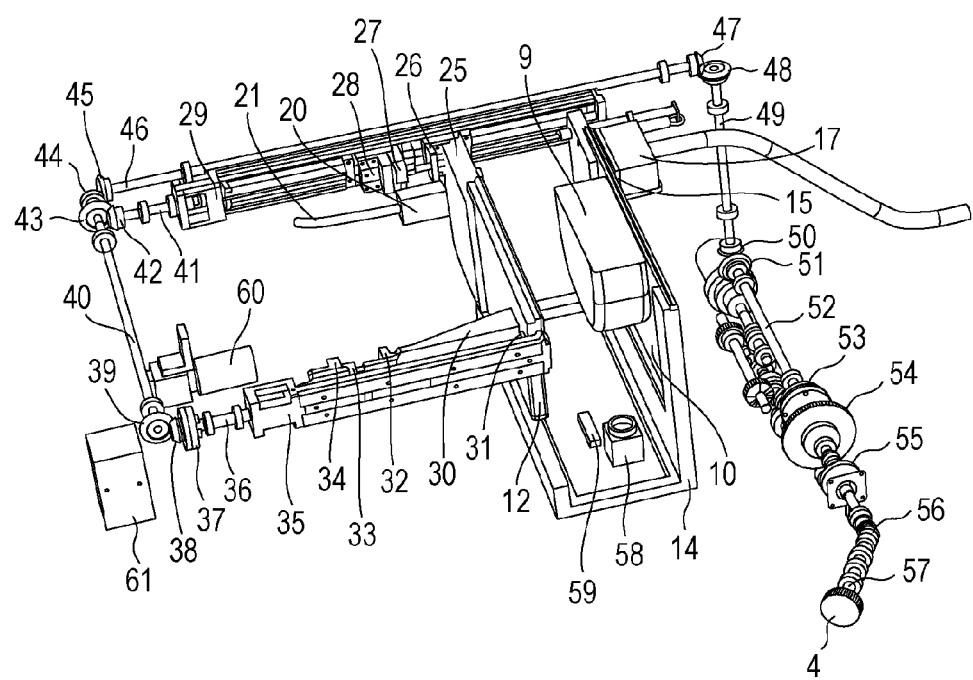
FIG. 12 is a perspective view of the compression mechanism.
Figure 13:
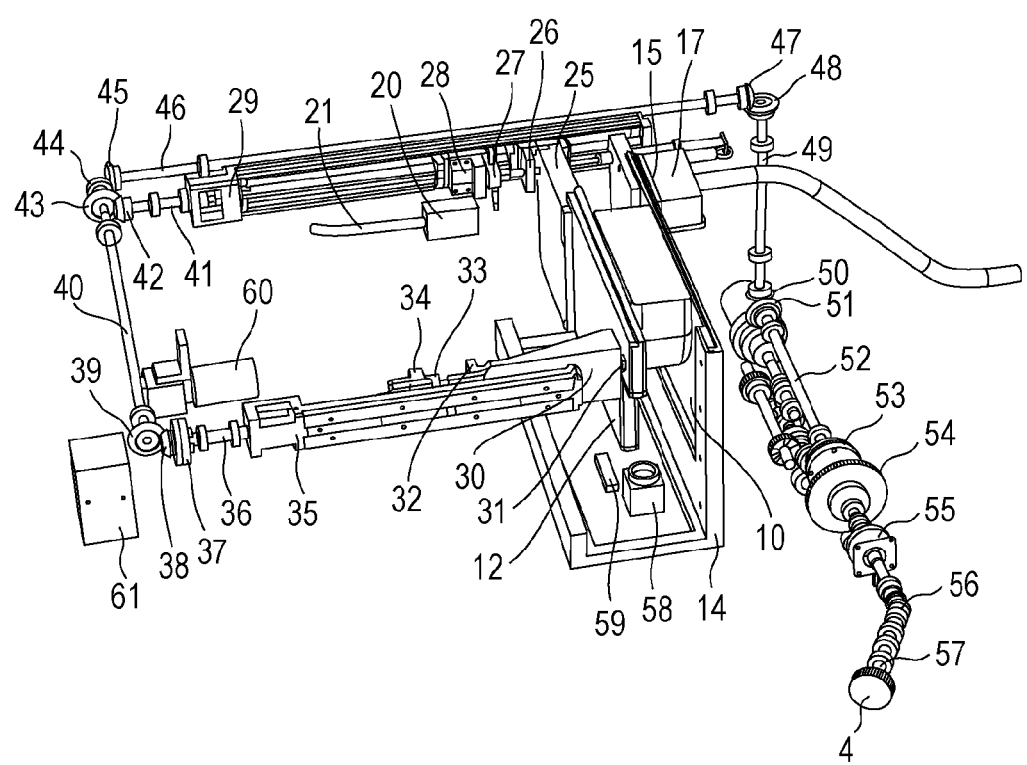
FIG. 13 is a perspective view of the compression mechanism.
Figure 14:
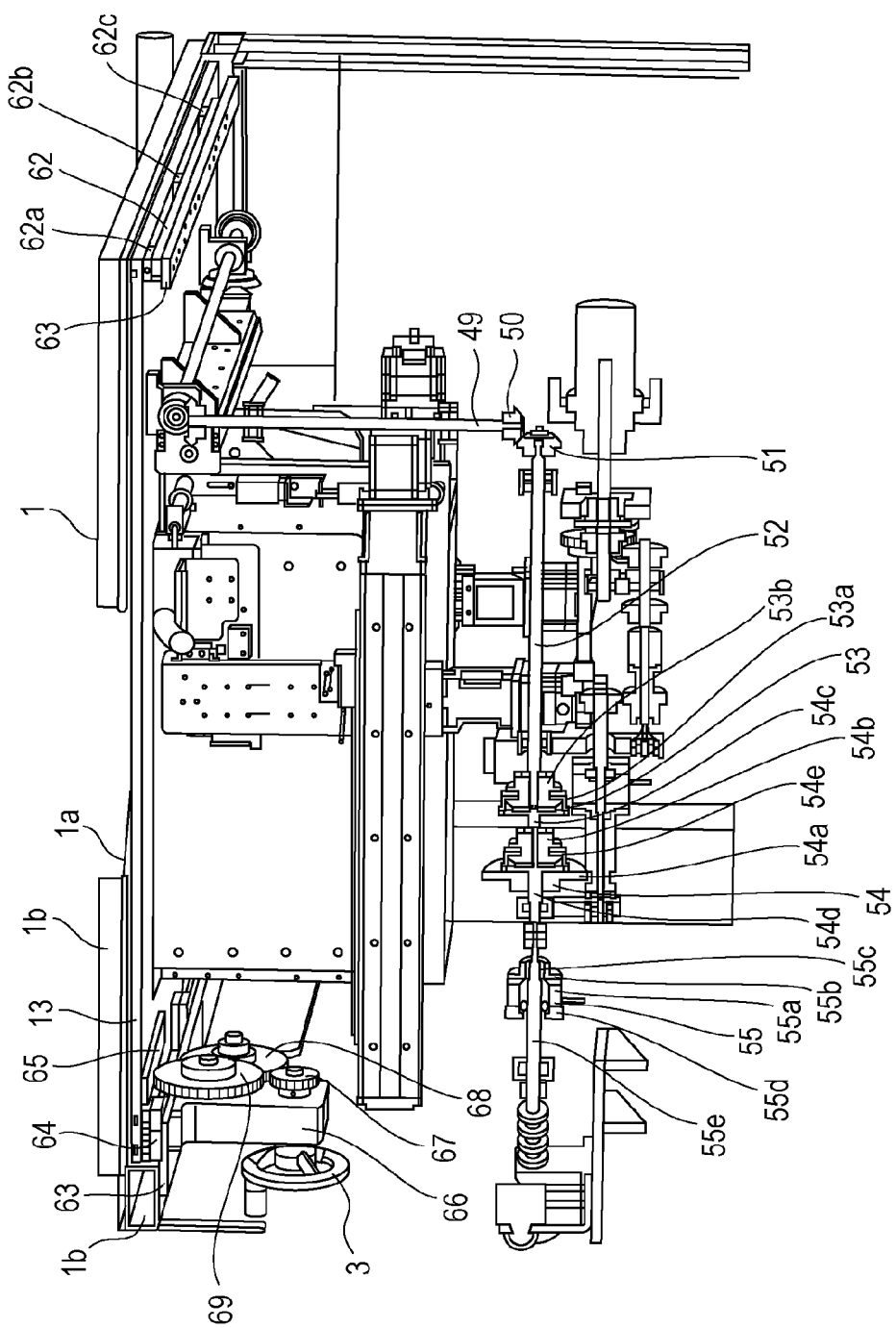
FIG. 14 is a perspective view of the compression mechanism.
Figure 15:
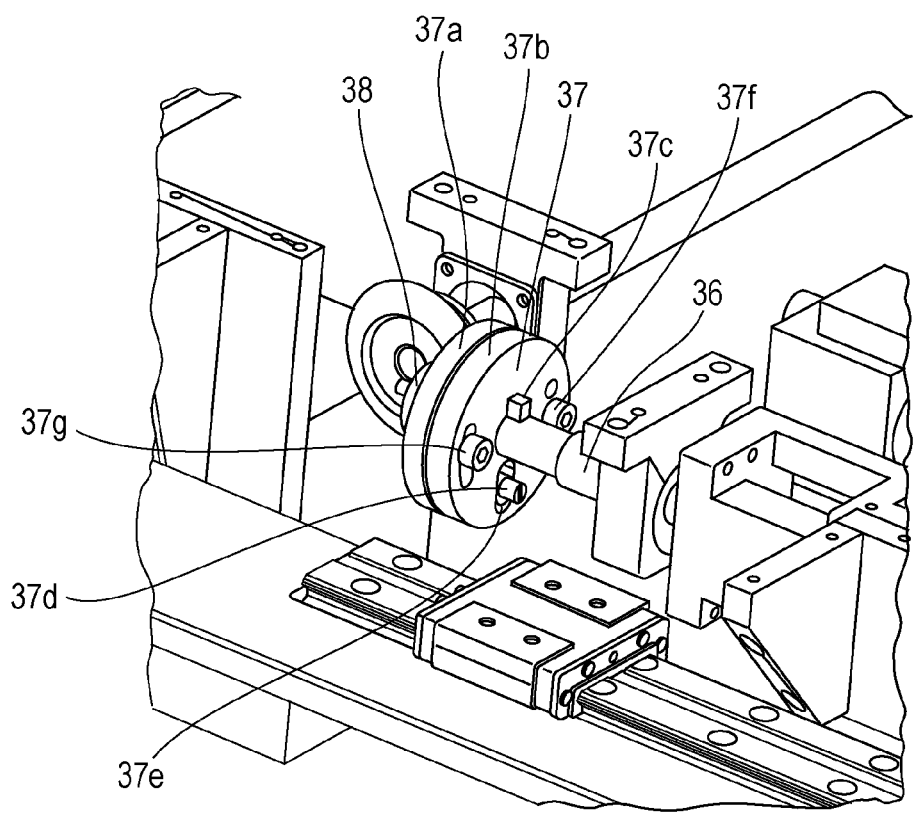
FIG. 15 is a partial perspective view of the compression mechanism.

Next, a compression mechanism is described. FIGS. 9 and 12 to 15 are illustrations showing a compression mechanism according to the embodiment of the present invention. FIG. 9 illustrates arrangement of both compression mechanism and scanning mechanism. FIGS. 12 and 13 are perspective views extracting only parts relating to compression according to the embodiment of the present invention. FIGS. 12 and 13 omit illustration of the under tray 11, so that a monitor camera 58 and a LED illumination device 59 provided below the under tray 11 can be observed. FIG. 14 is a cross-sectional perspective view showing a mechanism that causes the compression measurement unit 2 to slide relative to the bed 1 through rotation of the slide handle 3, and a coupling mechanism of the manual compression handle. FIG. 15 is an enlarged view showing the detail of a phase adjustment plate.

In FIG. 9, the fixed compression plate 10 is fixed to the base plate 13 by a compression-plate guide 14. The under tray 11 is also mounted at the compression-plate guide 14. The under tray 11 is used during a manipulation when the breast of the subject is inserted from the bed 1 such that the breast is arranged along the fixed compression plate 10 with ultrasonic gel or water applied to the breast. That is, the under tray 11 is a tray that prevents the ultrasonic gel or water from being dropped on the monitor camera 58 and the LED illumination device 59.

In FIG. 12, reference sign 25 denotes a compression-plate holder that supports the movable compression plate 12 by screwing. The compression-plate holder 25 is fixed to a linear guide 26 of a linear guide body 29 and slides along the linear guide body 29. The linear guide body 29 allows a linear guide 28 to slide when a lead screw shaft 41 rotates. The linear guide 28 is fitted on the lead screw shaft 41 by a screw. In contrast, the linear guide 26 does not have inside thereof a fitting structure by a screw for the lead screw shaft 41. The linear guide 28 is coupled with the linear guide 26 through a pressure sensor 27. Accordingly, when the lead screw shaft 41 rotates, the linear guide 28 slides along the lead, and the linear guide 26 and the movable compression plate 12 also slide in the same direction. When the movable compression plate 12 slides to compress a breast or a breast phantom, a reactive force of the compression is generated at the movable compression plate 12, and the pressure sensor 27 can measure the compression force.

Reference sign 30 denotes a compression-plate one-side pressing lever that is fixed to a linear guide 32 and can slide on a linear guide body 35. A compression-plate one-side pressing knob 31 is set for the movable compression plate 12. The linear guide 32 does not have inside thereof a fitting structure by a screw for a lead screw shaft 36. The linear guide 32 is coupled with a linear guide 34 through a pressure sensor 33. When the lead screw shaft 36 rotates and the linear guide 34 slides relative to the linear guide body 35, the linear guide 32, the compression-plate one-side pressing lever 30, the compression-plate one-side pressing knob 31, and the movable compression plate 12 are pressed in a pressing direction through the pressure sensor 33.

The movable compression plate 12 is driven to slide by the linear guide bodies 29 and 35. However, due to parallelism between the linear guide bodies 29 and 35 and eccentricities of the linear guide bodies 29 and 35, if the movable compression plate 12 is fixed by the linear guide 26 and then is fixed by the linear guide 32, the movable compression plate 12 may be excessively restrained, and sliding may become difficult. Owing to this, the compression-plate one-side pressing knob 31 only contacts the movable compression plate 12 in the compression direction and is not fixed to the movable compression plate 12.

Reference sign 37 denotes a phase adjustment plate. As shown in FIG. 15, the phase adjustment plate 37 includes a driving plate 37a and a driven plate 37b. The driving plate 37a is integrally formed with a bevel gear 38 and is rotatably fitted on the lead screw shaft 36. The driving plate 37a is coupled with the driven plate 37b by screws 37g and 37f. Also, an eccentricity adjustment shaft 37d is rotatably coupled with the driving plate 37a. An eccentric portion of the eccentricity adjustment shaft 37d is fitted to a long hole 37e of the driven plate 37b. The driven plate 37b is fitted on the lead screw shaft 36 by a keyway. Since the driven plate 37b is coupled with the driving plate 37a by the screws 37g and 37f, a driving force of the bevel gear 38 is transmitted to the lead screw shaft 36.

Bevel gears 39 and 43 are fitted on a rotation shaft 40 through keys. When a bevel gear 44 is driven to rotate, the bevel gears 39 and 43 rotate together with the rotation shaft 40.

Bevel gears 45 and 47 are fitted on a rotation shaft 46 through keys, and rotate together with the rotation shaft 46. Bevel gears 48 and 50 are fitted on a rotation shaft 49 through keys, and rotate together with the rotation shaft 49.

Reference sign 51 denotes a bevel gear that is integrated with a rotation shaft 52 by a key. Reference sign 53 denotes a torque limiter. Reference sign 54 denotes a torque limiter with a coupling gear. These torque limiters slip with the same torque. This configuration is provided for safety in case of a breakdown during compression of a breast. Even if one of the torque limiters is broken and no longer slips, the other torque limiter can prevent excessive compression. The torque limiter 53 includes a friction spring between a rotor portion 53b into which the rotation shaft 52 is press-fitted and an outer portion 53a with which a rotation shaft 54c is coupled. If a rotating torque of the rotation shaft 54c exceeds a predetermined rotating torque, rotation is not transmitted from the outer portion 53a to the rotor portion 53b. Hence, a torque exceeding the predetermined torque is not generated on the rotation shaft 52.

The torque limiter 54 with the coupling gear has the same structure as the torque limiter 53. The torque limiter 54 includes a friction spring between a rotor portion 54b into which the rotation shaft 54c that is an output shaft is press-fitted and an outer portion 54e with which a rotation shaft 54d is coupled. If a rotating torque of the rotation shaft 54d exceeds a predetermined rotating torque, rotation is not transmitted from the outer portion 54e to the rotor portion 54b. Hence, a torque exceeding the predetermined torque is not generated on the rotation shaft 54c.

Also, a coupling gear portion 54a for transmission of electric driving is fixed to the rotation shaft 54d by press-fitting, and rotates together with the rotation shaft 54d. During electric driving, since power is transmitted through the portion with the double torque limiters when the breast is compressed, even if an electric drive mechanism is broken and provides driving with a torque equal to or higher than a predetermined torque, only compression by a predetermined degree or smaller can be provided.

Reference sign 55 denotes a brake with a one-way mechanism, the brake including a bearing 55d fixed to the compression measurement unit 2, and a stator 55a fixed to the bearing 55d by a screw or the like. An electromagnetic coil is provided in the stator 55a. The electromagnetic coil is magnetized when the electromagnetic coil is energized. The electromagnetic coil attracts a brake rotor 55b and unitizes the brake rotor 55b with the stator 55a. Accordingly, the brake works. The brake rotor 55b includes a one-way mechanism 55c and is coupled with a rotation shaft 55e through the one-way mechanism 55c. When the brake rotor 55b is unitized with the stator 55a by the magnetization of the stator 55a and hence the brake works, the rotation shaft 55e is allowed to rotate in a release direction of the one-way mechanism 55c but is inhibited from rotating in a lock direction of the one-way mechanism 55c. This explanation is for an operation when the state change switch 5 changes the state of rotation of the manual compression handle 4 to the one-way latch state.

In particular, the manual compression handle 4 is rotatable when the manual compression handle 4 is rotated in the compression direction of the movable compression plate 12, and the manual compression handle 4 is locked and non-rotatable when the manual compression handle 4 is rotated in the release direction of the movable compression plate 12.

As described above, since the rotation of the manual compression handle 4 is locked when the manual compression handle 4 is rotated in the release direction of the movable compression plate 12, a reactive force when the movable compression plate 12 compresses a breast is not generated on the manual compression handle 4. The operator does not have to always grip the manual compression handle 4 during compression, and the operation becomes easy. Also, when the state change switch 5 changes the state to the constantly direct-coupled state, the electromagnetic coil in the stator 55*a* is no longer energized, and magnetization is no longer provided. The brake rotor 55*b* is separated from the stator 55*a*, and the one-way mechanism 55*c* no longer works. Accordingly, the manual compression handle 4 becomes freely rotatable in the compression direction and the release direction.

Reference sign 56 denotes a universal joint that couples the rotation shaft 55*e* with a rotation shaft 57 of the manual compression handle 4 at an angle of about 30 degrees. The rotation shafts 52, 54*c*, 54*d*, and 55*e* for compression and release are substantially linearly arranged from the far side toward the near side. By mounting the manual compression handle 4 with the inclination by the angle of about 30 degrees with respect to the manipulation opening 2*a* for a manipulation, the handle can be most easily operated for compression or release at that position during a manipulation.

Phase adjustment is setting such that the movable compression plate 12 fixed to and supported by the linear guide 26 at a position determined by the lead screw shaft 41 of the linear guide body 29 contacts the compression-plate one-side pressing knob 31 at a position at which the movable compression plate 12 is located at a plane parallel to the fixed compression plate 10. To set the compression-plate one-side pressing knob 31 at the contact position with respect to the movable compression plate 12, the eccentricity adjustment shaft 37*d* is rotated while the screw 37*g* of the phase adjustment plate 37 is loosened, and simultaneously, a rotation phase of the lead screw shaft 36 is changed with respect to a phase of the bevel gear 38 determined by the bevel gears 39 and 43. Hence, the linear guide 34 is finely adjusted by sliding with respect to the linear guide body 29 by a value of lead/rotation angle of the lead screw shaft 36. Thus, the contact position of the compression-plate one-side pressing knob 31 with respect to the movable compression plate 12 is adjusted.

In the acoustic-wave acquiring apparatus according to the embodiment of the present invention, the compression plate is supported by the two shafts, and such a fine adjustment mechanism is installed in view of the parallelism between the fixed compression plate 10 and the movable compression plate 12. In X-ray mammography, a compression plate performs compression while being supported typically by a single member. The X-ray mammography provides a projection image obtained by measuring transmission of X-rays from the upper side of a compressed breast. The projection image is an image in a flat plane. Compression is performed to increase the transmittance for X-rays and minimize the amount of X-rays, thereby preventing the subject from being excessively exposed to X-rays. Also, compression is performed to expand the breast as possible and reduce an overlap in the projection image. As the result, the parallelism between the compression plates is not a serious matter, and hence the compression plates are frequently supported by the single shaft.

In contrast, in the acoustic-wave acquiring apparatus according to the embodiment of the present invention, illumination is provided with laser light, an ultrasonic wave of hemoglobin in blood is measured, and a location of the hemoglobin is reconstructed by calculation, to determine the location of the ultrasonic wave in the three-dimensional space of the breast. In this case, if an acoustic-wave property of the ultrasonic wave of the breast is obtained, the calculation can be performed. However, an acoustic property of an ultrasonic wave of a human body varies in a complicated manner. It is difficult to measure the acoustic-wave property. In this situation, if the parallelism between the compression plates is very accurately set, the position of the ultrasonic wave generated from the hemoglobin can be figured out with reference to the compression plates. Even though the acoustic-wave property of the ultrasonic wave of the human body is uncertain, the level of cluster in blood, such as a cancer, can be calculated. Accordingly, in the acoustic-wave acquiring apparatus according to the embodiment of the present invention, the movable compression plate 12 is supported by the two shafts, and a countermeasure that adjusts the parallelism between the movable compression plate 12 and the fixed compression plate 10 is required.

Figure 16:
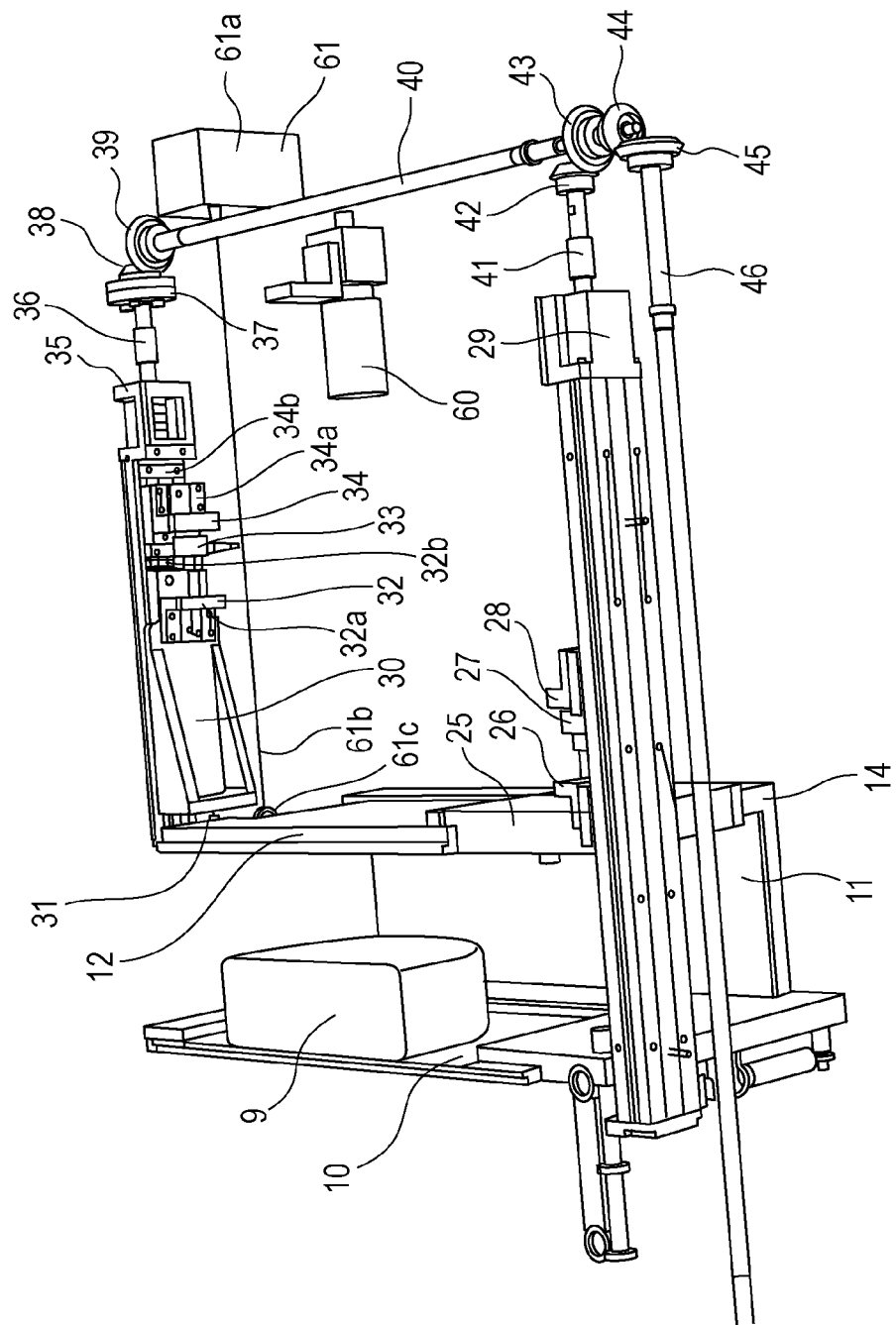
FIG. 16 is a perspective view of the compression mechanism.
Figure 17:
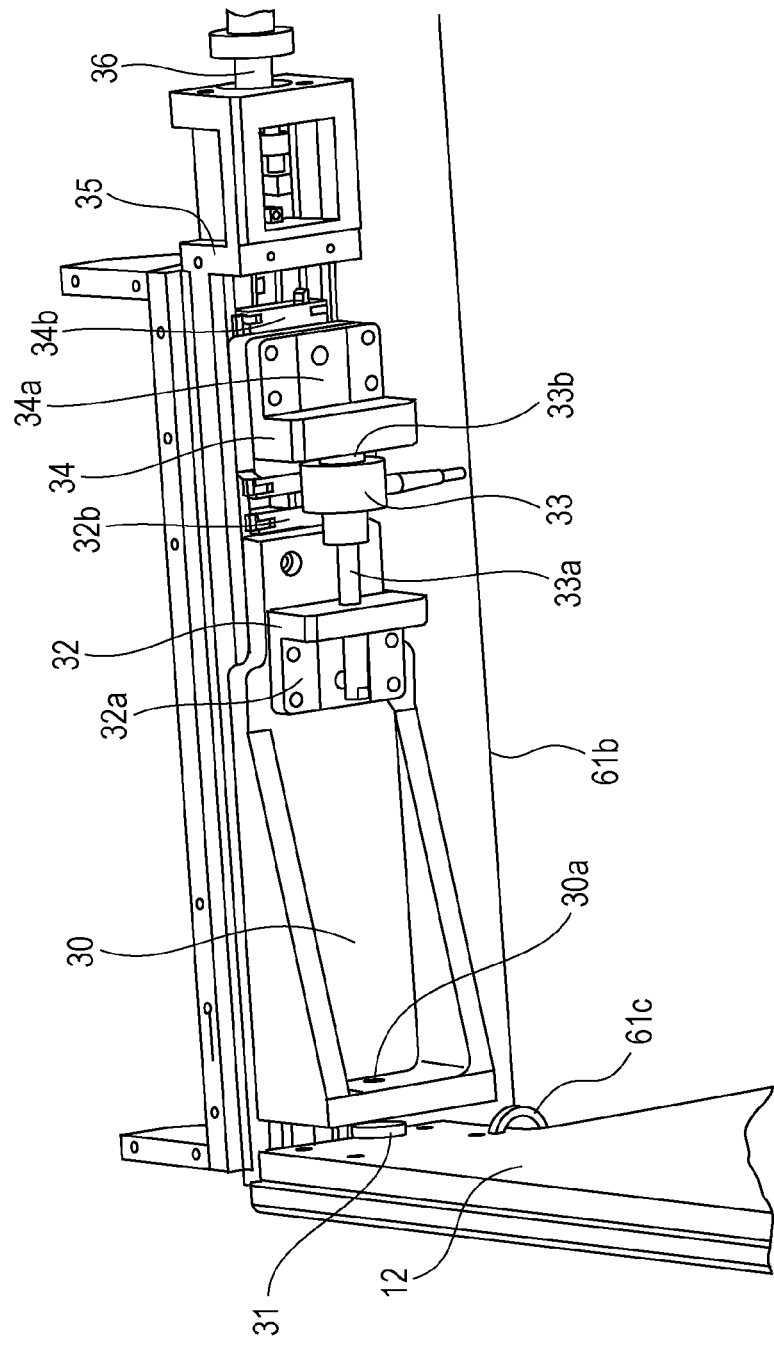
FIG. 17 is a partial perspective view of the compression mechanism.

FIGS. 16 and 17 are illustrations showing the detail of the compression mechanism according to the embodiment of the present invention. In FIG. 16, reference sign 61 denotes a potentiometer. A hook portion 61*c* of the potentiometer 61 is fixed to the movable compression plate 12, and the potentiometer 61 is coupled with the hook portion 61*c* by a wire 61*b* pulled from a body 61*a* of the potentiometer 61. Accordingly, a compression moving distance of the movable compression plate 12 is calculated by using a length of the wire 61*b* pulled from the body 61*a*. FIG. 17 is a perspective view showing the detail of the one-side pressing portion of the movable compression plate 12. The phase adjustment of the pressing portion of the movable compression plate 12 can be performed by the fine adjustment by the phase adjustment plate 37 as described above. Described below is an embodiment, in which an adjustment amount that cannot be provided by the fine adjustment is required.

First, the pressing portion of the movable compression plate 12 slides by a lead fitting portion of a lead piece portion 34*b* of the linear guide 34 by rotating the lead screw shaft 36. The pressing portion of the movable compression plate 12 is fixed to a mount 34*a* of the linear guide 34 by a mount portion 33*b* of the pressure sensor 33. A mounting bolt 33*a* is mounted at the other end of the pressure sensor 33. If a mount 32*a* fixed to a linear guide 32*b* that is not fitted on the lead screw shaft 36 through a lead is coupled with the other end of the mounting bolt 33*a* by a nut or the like, a slide driving force can be transmitted therebetween. Further, the compression-plate one-side pressing lever 30 is fixed to the lead piece portion 34*b* of the linear guide 34. The compression-plate one-side pressing knob 31 is located at the other end of the compression-plate one-side pressing lever 30 and screwed into a screw tap portion 30*a*.

The compression-plate one-side pressing knob 31 presses the movable compression plate 12 in this state. Hence, by changing the screwing amount of the compression-plate one-side pressing knob 31 with respect to the compression-plate one-side pressing lever 30, parallel pressing adjustment of the movable compression plate 12 can be performed similarly to when the driving phase of the lead screw shaft is changed.

Also, the parallel pressing adjustment of the movable compression plate 12 can be performed similarly to when the driving phase of the lead screw shaft is changed, even if the position of the nut that mounts the mounting bolt 33*a* of the pressure sensor 33 onto the mount 32*a* is changed. However, since the target to be adjusted is a normal bolt or a normal screw portion, the parallel pressing adjustment of the movable compression plate 12 is adjustment by a large distance, but is not fine adjustment. Hence, a fine adjustment mechanism by the phase adjustment plate 37 is required.

Electric Drive Mechanism

Figure 18:
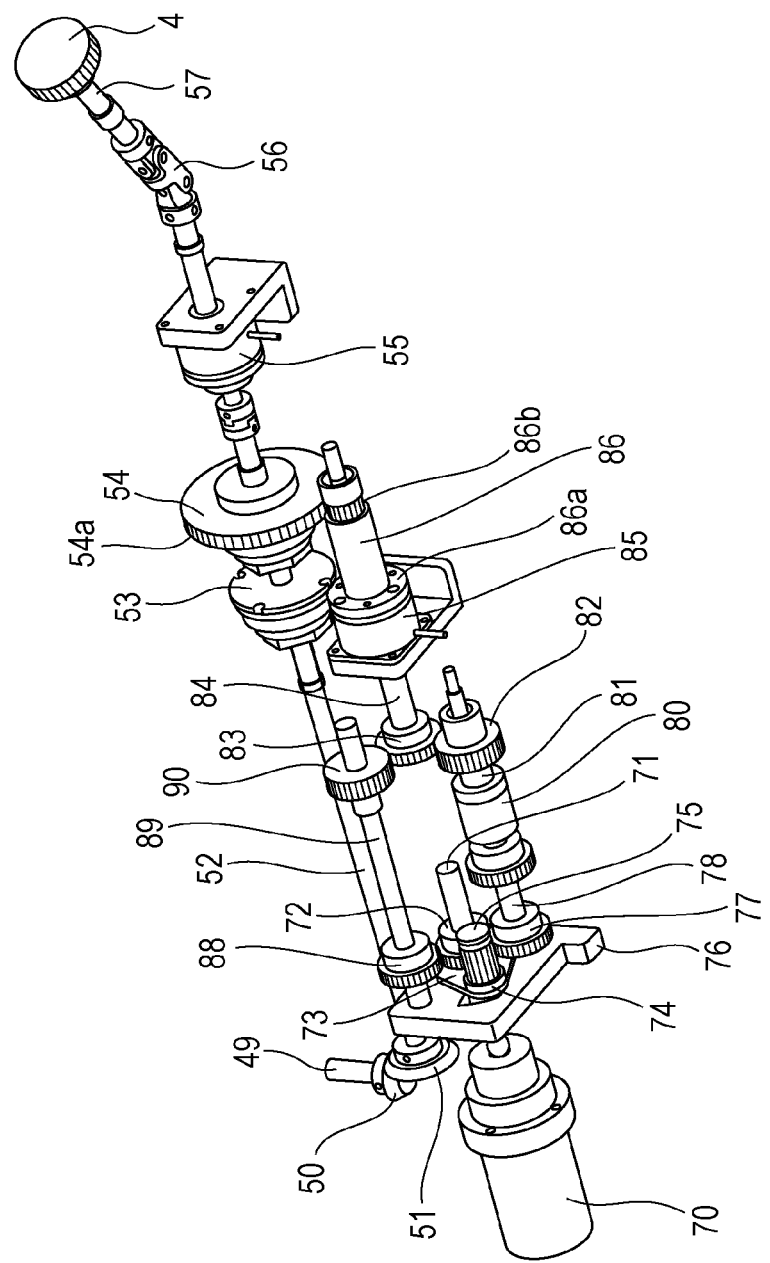
FIG. 18 is a perspective view of an electric compression mechanism.

Next, an electric drive mechanism for compression is described. FIGS. 18 to 21 are operation explanatory views of an electric compression mechanism according to the embodiment of the present invention. In FIG. 18, reference sign 70 denotes an electric drive motor that supplies power when the foot pedal 6 in FIG. 1 is depressed and turned ON. When the pedal 6*b* is depressed and turned ON, a motor output shaft 71 rotates counterclockwise to provide driving in the compression direction. When the pedal 6*a* is depressed and turned ON, the motor output shaft 71 rotates clockwise to provide driving in the release direction. Reference sign 72 denotes a planetary-gear-change sun gear that is fitted on the motor output shaft 71 by a key and rotates together with the motor output shaft.

Figure 19:
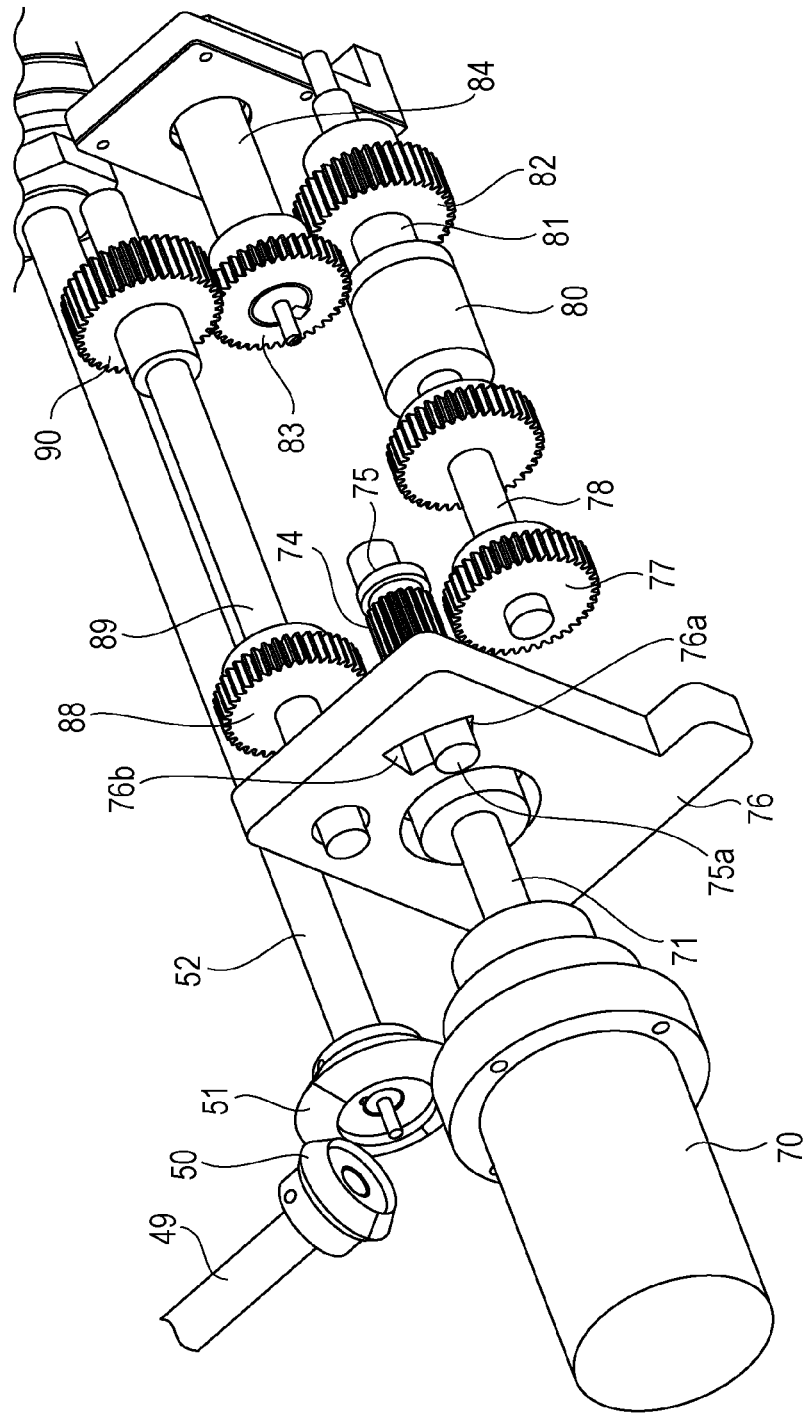
FIG. 19 is a partial perspective view of the electric compression mechanism.

Reference sign 73 denotes a planetary-gear change lever that is rotatably fitted on the motor output shaft 71. A friction spring is provided between the planetary-gear change lever 73 and the sun gear 72, and an urging force acts therebetween. Hence, the planetary-gear change lever 73 rotates in the same direction as that of the motor output shaft 71. Reference sign 74 denotes a planetary gear rotatably fitted on a planetary gear shaft 75 that is fixed to the planetary-gear change lever 73 by press-fitting. The planetary gear shaft 75 fixed to the planetary-gear change lever 73 by press-fitting has a stopper pin 75*a* that protrudes further from the planetary-gear change lever 73 as shown in FIG. 19. The stopper pin 75*a* contacts a compression-driving planetary-gear stopper surface 76*a* and a release-driving planetary-gear stopper surface 76*b* of a planetary-gear change plate 76, for positioning the planetary gear 74.

In FIG. 19, when the motor output shaft 71 rotates clockwise, the sun gear 72 rotates clockwise, and the planetary-gear change lever 73 also rotates clockwise. Then, the stopper pin 75*a* of the planetary gear shaft 75 contacts the compression-driving planetary-gear stopper surface 76*a* of the planetary-gear change plate 76 and the clockwise rotation of the planetary-gear change lever 73 is stopped. The position at which the clockwise rotation of the planetary-gear change lever 73 is stopped is a position at which the planetary gear 74 meshes with a gear 77. Even when the stopper pin 75*a* contacts the compression-driving planetary-gear stopper surface 76*a* of the planetary-gear change plate 76 and the clockwise rotation of the planetary-gear change lever 73 is stopped, since the sun gear 72 slips by the friction spring (not shown), the sun gear 72 can transmit power that is reduced by a slipping torque of the friction spring. Thus, the rotation of the sun gear 72 is transmitted from the planetary gear 74 to the gear 77, and a rotation shaft 78 that is fitted to the gear 77 by a key and rotated together with the gear 77 rotates clockwise.

Reference sign 80 denotes a torque limiter that transmits the rotating torque of the rotation shaft 78 to a rotation shaft 81. If the rotating torque of the rotation shaft 78 becomes a predetermined level or higher, the rotation shaft 78 rotates at idle. The torque limiter 80 limits an upper limit value of the rotating torque of the rotation shaft 81. A gear 82 is fitted on the rotation shaft 81 by a key and rotates together with the rotation shaft 81. The gear 82 constantly meshes with a gear 83. The gear 83 is fitted on a rotation shaft 84 by a key and rotates together with the rotation shaft 84. The rotation shaft 84 also rotates together with a clutch plate (not shown) provided in a clutch 85. The clutch plate is electromagnetically attracted to an armature portion 86*a* of a clutch rotor 86 when the clutch 85 is energized, and the clutch plate becomes rotatable together with the armature portion 86*a*. The clutch plate can transmit the rotating torque of the rotation shaft 84 to a sleeve gear 86*b* of the clutch rotor 86.

When application of electricity to the clutch rotor 86 is stopped, the electromagnetic attraction between the clutch plate coupled to the rotation shaft 84 and the armature portion 86*a* of the clutch rotor 86 is eliminated, and the rotating torque of the rotation shaft 84 is not transmitted to the clutch rotor 86. The sleeve gear 86*b* of the clutch rotor 86 constantly meshes with the coupling gear portion 54*a* of the torque limiter 54 with the coupling gear. Hence, when the rotating torque of the electric drive motor 70 is transmitted to the clutch rotor 86, the coupling gear portion 54*a* rotates, and electric compression driving is started.

Figure 20:
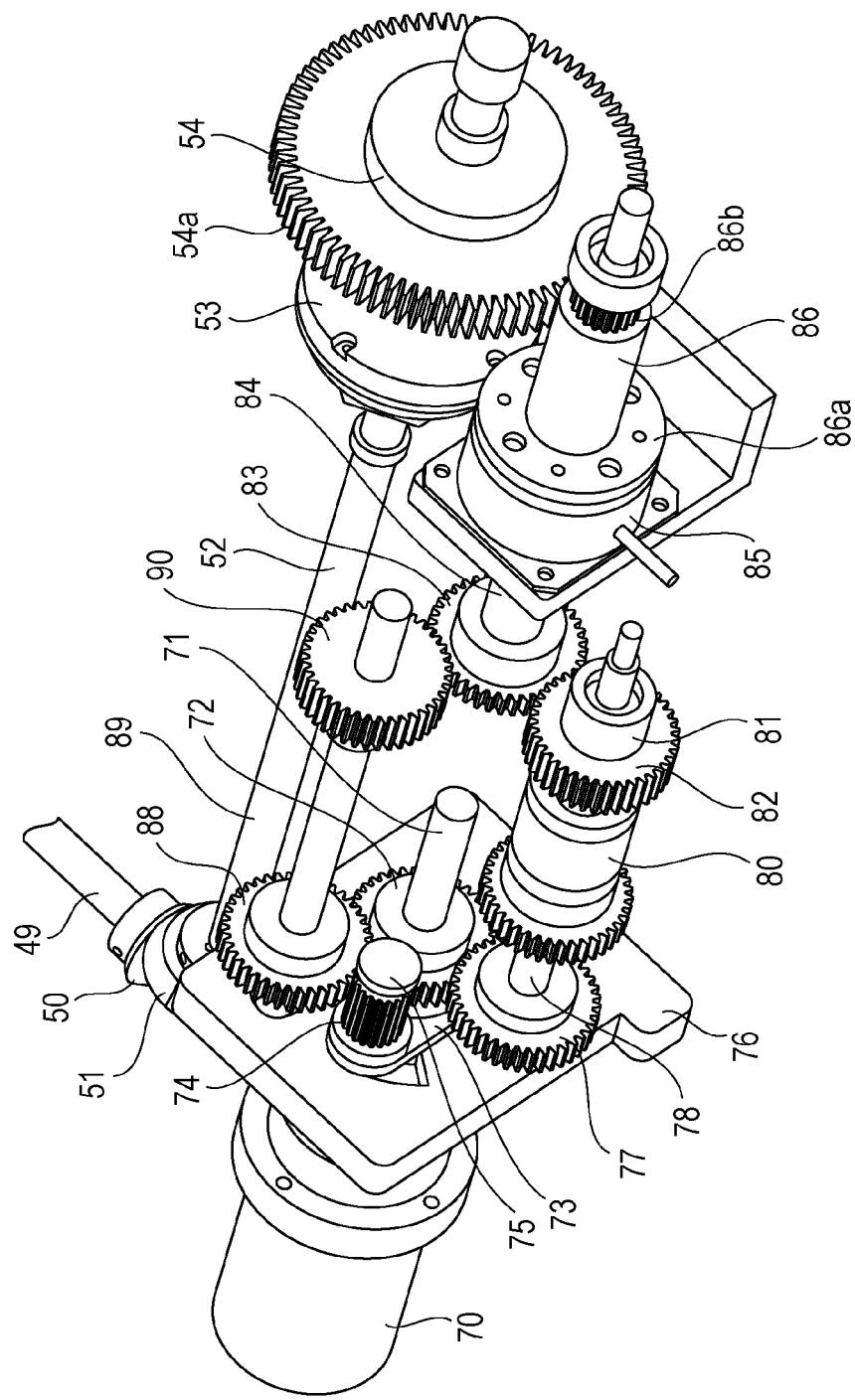
FIG. 20 is a partial perspective view of the electric compression mechanism.
Figure 21:
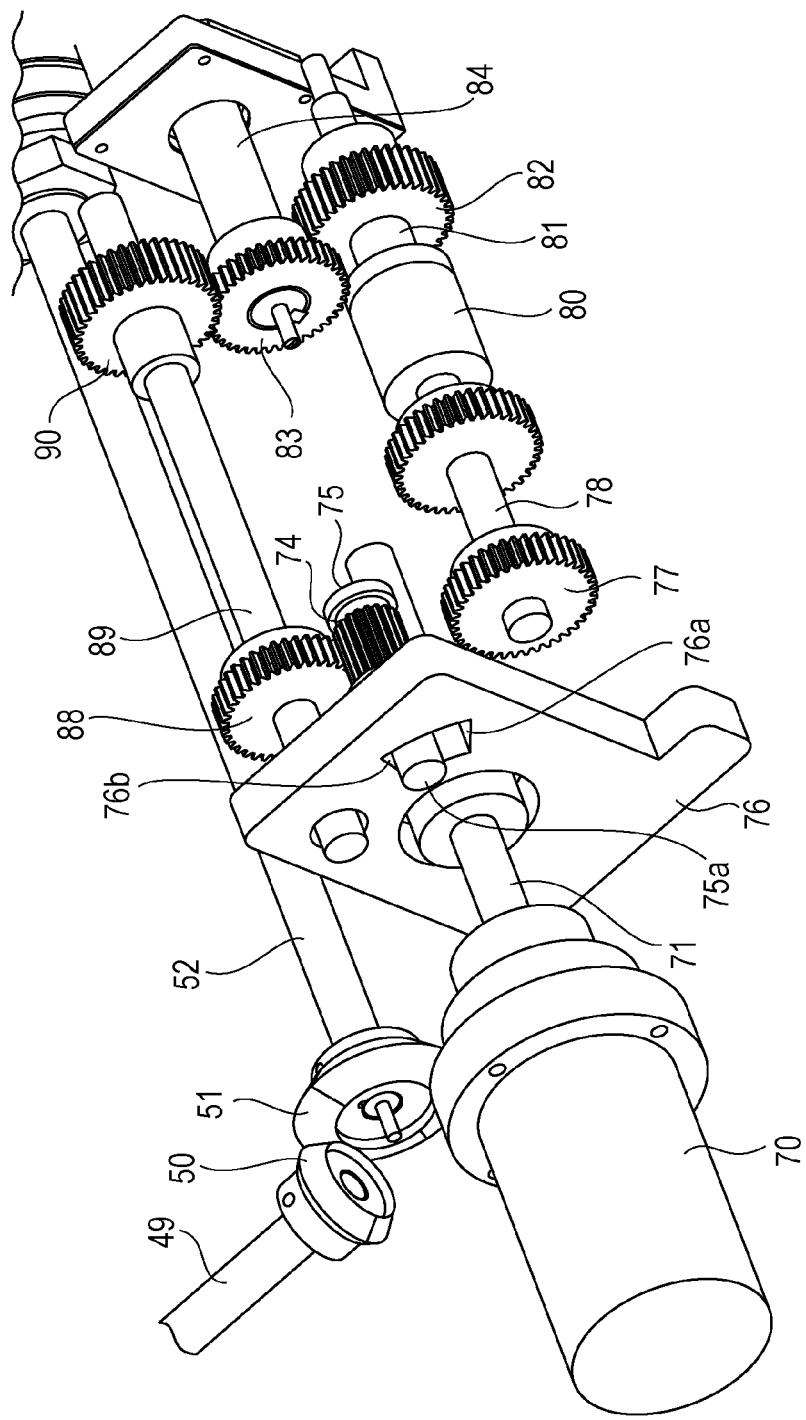
FIG. 21 is a partial perspective view of the electric compression mechanism.

In FIG. 20, when the pedal 6*a* in FIG. 1 is depressed and turned ON, the motor output shaft 71 of the electric drive motor 70 rotates clockwise for driving in the release direction. Then, the sun gear 72 rotates clockwise, and hence the planetary-gear change lever 73 rotates clockwise by the friction spring of the sun gear 72. The stopper pin 75*a* of the planetary gear shaft 75 contacts the release-driving planetary-gear stopper surface 76*b* of the planetary-gear change plate 76. This state is shown in FIGS. 20 and 21.

When the stopper pin 75*a* contacts the release-driving planetary-gear stopper surface 76*b*, the rotation of the sun gear 72 is transmitted to the planetary gear 74, and the planetary gear 74 meshes with a gear 88. When the stopper pin 75*a* contacts, the rotation of the planetary-gear change lever 73 stops such that the contact state of the stopper pin 75*a* is maintained while a clockwise rotating force from the friction spring of the sun gear 72 slips. The gear 88 is fitted on a rotation shaft 89 by a key and rotates together with the rotation shaft 89. The rotation shaft 89 is also fitted to a gear 90 by a key. Hence, the rotating torque of the gear 88 is directly transmitted to the gear 90. The gear 90 meshes with the gear 83 and the rotating torque of the gear 90 is transmitted to the clutch 85. Transmission of the rotating torque to the clutch 85 and downstream portions is similar to transmission for the above-described compression driving.

Slide Mechanism

Next, sliding is described. In FIG. 14, slide-rail receiving plates 63 are fastened to a frame 1*b* of the bed 1 by screws or the like. Slide rails 62 and 64 are mounted on the slide-rail receiving plates 63. The base plate 13 is arranged on pieces 62*a*, 62*b*, and 62*c* sliding on the slide rail 62 and pieces sliding on the slide rail 64, and the base plate 13 is fastened to the pieces of the slide rails 62 and 64 by screws or the like. With this configuration, the base plate 13 can slide relative to the bed 1 along the slide rails 62 and 64. Slide driving is made when the slide handle 3 is rotated.

In FIG. 14, the slide handle 3 is directly coupled with a handle gear 67 through a rotation shaft included in a handle holder 66 and rotates together with the handle gear 67. The handle gear 67 meshes with a reduction gear 68. The reduction gear 68 meshes with a slide drive gear 69. The reduction gear 68 and the slide drive gear 69 are rotatably supported on shafts fixed to the handle holder 66.

Further, the slide drive gear 69 meshes with a slide rack gear 65 fixed to the base plate 13. Hence, in FIG. 14, when the slide handle 3 is rotated clockwise, the handle gear 67 also rotates clockwise, and the reduction gear 68 rotates counterclockwise. Since the slide drive gear 69 rotates clockwise, the slide drive gear 69 drives the slide rack gear 65 to slide rightward, and the base plate 13 also slides rightward. At least the fixed compression plate 10 is hung from the base plate 13. Hence, this sliding direction corresponds to an under-breast pre-compression operation of an inserted breast (described later).

Also, when the slide handle 3 is rotated counterclockwise, the base plate 13 slides leftward in a reverse direction, so that the under-breast pre-compression of the breast can be released.

Operation of Manual Mechanism

Next, an operation of a manual mechanism is described. In FIG. 12, when the manual compression handle 4 is rotated counterclockwise, the movable compression plate 12 approaches the fixed compression plate 10, thereby providing a compression operation. To be more specific, when the manual compression handle 4 is rotated counterclockwise, the rotation is transmitted to the rotation shaft 57 and reaches the brake 55 with the one-way mechanism through the universal joint 56. The brake 55 with the one-way mechanism acts when the state change switch 5 in FIG. 1 selects the one-way latch state. In contrast, when the manual compression handle 4 is rotated counterclockwise in the compression direction, since the rotation is in a free-rotation direction of the one-way mechanism, a rotation load is not generated, and the rotation is transmitted to the downstream torque limiter 54 with the coupling gear.

The coupling gear portion 54a of the torque limiter 54 with the coupling gear constantly meshes with the sleeve gear 86b of the clutch 85. However, when the foot pedal 6 in FIG. 1 is not depressed, the clutch 85 in FIG. 18 is not coupled with the coupling gear portion 54a or the electric drive motor 70. Accordingly, a rotation load is not generated. If the rotating torque from the manual compression handle 4 at the input side exceeds 300 N when the rotating torque is converted into a pressing force for pressing the movable compression plate 12, the torque limiter portion of the torque limiter 54 with the coupling gear controls the force generated at an input shaft of the torque limiter 53 at the output side so as not to exceed 300 N.

Also, the torque limiter 53 serves as the same torque limiter as the torque limiter 54 with the coupling gear, and controls the output rotating torque with respect to the input rotating torque so as not to exceed 300 N when the rotating torque is converted into the pressing force for pressing the movable compression plate 12. The double torque limiters are provided for a certification in case of a failure of a single torque limiter. Even if one of the torque limiters is broken, it can be certified that the rotating torque does not exceed 300 N when the rotating torque is converted into a pressing force for the movable compression plate 12. Since the electric driving torque is transmitted from the coupling gear portion 54a during electric compression with the electric drive motor 70, this safety mechanism also certifies a system such that the rotating torque does not exceed 300 N.

The manual compression force transmitted to the rotation shaft 52 that is the output shaft of the torque limiter 53 is transmitted to the bevel gears 51 and 50 to change the direction. Then, the direction of the force is changed at the bevel gears 48 and 47 shown in FIG. 13 in association with the rotation shaft 49 and is transmitted to the rotation shaft 46. Then, the force is transmitted to the rotation shaft 40 from the bevel gears 45 and 44. The two bevel gears 43 and 39 are fitted on the rotation shaft 40 by keys and rotate together with the rotation shaft 40. Accordingly, the left and right linear guide bodies 29 and 35 of the movable compression plate 12 can be simultaneously driven. Also, when the movable compression plate 12 provides compression, the movable compression plate 12 can be constantly parallel to the fixed compression plate 10 regardless of the position of the breast.

The rotating torque transmitted to a bevel gear 42 that meshes with the bevel gear 43 is transmitted to the lead screw shaft 41 that is fitted to the bevel gear 42 by a key and rotates together with the bevel gear 42. The rotating torque generates a rightward moving force at the linear guide 28 that is fitted on the lead screw shaft 41 by a screw. Thus, a force for pressing rightward the linear guide 26 that is not fitted on the lead screw shaft 41 by a screw is generated through the pressure sensor 27 that measures the compression reactive force of the movable compression plate 12.

The compression-plate holder 25 of the movable compression plate 12 is rigidly directly mounted at the linear guide 26. The parallelism between the movable compression plate 12 and the fixed compression plate 10 can be sufficiently satisfied even with only the support by the linear guide 26. Owing to this, the rail portion of the linear guide body 29 also extends toward the fixed compression plate 10.

Meanwhile, the bevel gear 39 meshes with the bevel gear 38, and is driven simultaneously with the bevel gear 42, so that the movable compression plate 12 is pressed from the left and right sides. In this situation, it is very difficult to eliminate a gear phase shift between the bevel gears and to eliminate a phase difference between the lead screw shafts 41 and 36. Thus, according to the embodiment of the present invention, the phase adjustment plate 37 is provided. The phase adjustment plate 37 adjusts the phases such that the phase of the lead screw shaft 41 is fixed as a certified value because the fixed portion of the compression plate at the left side is provided and the phase of the lead screw shaft 36 is variable. That is, the phase adjustment plate 37 is provided on the shaft of the bevel gear 38 that meshes with the bevel gear 39. The position after the phase adjustment is transmitted to the lead screw shaft 36, so that the linear guide 34 that is fitted on the lead screw shaft 36 by a screw is driven in the compression direction.

The pressure sensor 33 is mounted on the linear guide 34. The linear guide 32 that is not fitted on the lead screw shaft 36 by a screw is pressed in the compression direction through the pressure sensor 33. When a breast is compressed, the breast has to be supported by a manipulation at a position of the linear guide body 35 near the compression plate. If the linear guide body 35 extends to the position of the fixed compression plate 10 like the left linear guide body 29, the linear guide body 35 may disturb the manipulation. It has been found through an experiment that the linear guide body 35 does not disturb the manipulation as long as the linear guide body 35 extends by a length to the same plane as a plane containing a maximum opening position of the movable compression plate 12 shown in FIG. 12.

Hence, if the linear guide body 35 extends to the maximum opening position of the movable compression plate 12, in order to press the movable compression plate 12 to a position near the fixed compression plate 10 at the position of the linear guide 34 or 32, the compression-plate one-side pressing lever 30 with an overhang shape is required. Also, when the movable compression plate 12 moves substantially in parallel to the fixed compression plate 10 for compression, the linear guide bodies 29 and 35 guide the movable compression plate 12. However, if the movable compression plate 12 is rigidly supported by the linear guide bodies 29 and 35, the movable compression plate 12 may be excessively restrained. That is, a load on the linear guides 26 and 28 or a load on the linear guides 32 and 34 may become very large. Hence, the support at the linear guide body 35 by supporting with the overhang shape only receives the compression reactive force that is generated when the movable compression plate 12 compresses the breast.

Accordingly, the linear guide body 35 of the movable compression plate 12 extends to the opening for the manipulation so as not to disturb the manipulation. Since the compression-plate one-side pressing lever 30 has an overhang shape, the compression plate can be driven along the two shafts. The parallelism with respect to the fixed compression plate 10 can be precisely maintained.

Operation of Electric Mechanism

Next, an operation of an electric mechanism is described. The electric compression mechanism is activated only when the foot pedal 6 in FIG. 1 is depressed. When the pedal 6b for driving in the compression direction of the foot pedal 6 in FIG. 1 is depressed, the electric drive motor 70 in FIG. 18 is energized to rotate counterclockwise, and the clutch 85 is also energized. Accordingly, the torque of the electric drive motor can be transmitted to the torque limiter 54 with the coupling gear. The electric torque is transmitted from the sun gear 72 to the gear 77 through the planetary gear 74, and is input from the planetary gear shaft 75 to the torque limiter 80.

The torque limiter 80 performs torque limitation in a manner different from those of the double torque limiters 54 and 53 provided in the manual compression mechanism. The electric compression and the manual compression are provided in X-ray mammography. A compression force of the electric compression is relatively small. Japan Industrial Standard (JIS) defines that the electric compression is used in an auxiliary manner. Owing to this, similarly in the mechanism according to the embodiment of the present invention, the compression force of the electric compression is relatively smaller than that of the manual compression. The electric compression force at the torque limiter 80 is set as about 70 N. Even if the electric drive motor is broken, a force with 70 N or larger slips and is not transmitted to the movable compression plate 12.

Regarding a certification for the electric compression mechanism in case of a failure of a single torque limiter, if the torque limiter 80 is broken, is directly coupled, and no longer provides the torque limitation, the torque is transmitted from the gear 82, the gear 83, the clutch 85, the sleeve gear 86b, and then to the coupling gear portion 54a, and is limited by the manual torque limiter with the limitation of 300 N. Thus, safety is certified.

If a compression force with 70 N or larger is generated during electric driving, an emergency stop button (not shown) is pressed, so that application of electricity to the electric drive motor is stopped. Also, application of electricity to the clutch 85 is stopped, so that the torque of the electric drive motor 70 is no longer transmitted to the sleeve gear 86b. Safety can be sufficiently assured.

Also, when the pedal 6b is depressed and the manual compression is further performed during the compression in the electric compression mode, if the coupling gear portion 54a is manually rotated counterclockwise in the gear coupling state shown in FIG. 18 faster than the electric compression, the sleeve gear 86b and the gear 83 rotate clockwise, and the coupled gear 82 rotates counterclockwise. Then, the torque limiter 80 and the gear 77 also rotate counterclockwise. When the gear 77 rotates counterclockwise, the planetary gear 74 repels the rotation, and a load on the manual compression handle 4 is not increased. In addition to driving in the electric compression direction, even if the pedal 6a for driving in the release direction of the foot pedal 6 is depressed and the movable compression plate 12 is electrically driven in the release direction, additional release driving can be provided by the manual compression handle. This configuration is described with reference to FIG. 20.

FIG. 20 illustrates a state in which the pedal 6a for driving in the release direction is depressed and hence electric release driving is provided. In this driving state, in order to move the manual compression handle 4 in the release direction of the movable compression plate 12, the manual compression handle 4 is rotated clockwise. Accordingly, the coupling gear portion 54a rotates clockwise, and the sleeve gear 86b and the gear 83 rotate counterclockwise. Further, the gear 90 and the gear 88 rotate clockwise. When the gear 88 rotates clockwise, similarly to the situation in which the additional manual rotation is made during compression, the planetary gear 74 repels the rotation, and the clockwise additional rotation of the gear 88 does not affect the electric drive motor 70.

Hence, even when the pedal 6a for driving in the release direction is depressed and the electric release operation is carried out, the additional release driving by the manual compression handle 4 does not receive a load. If the subject feels discomfort or an abnormal situation occurs during measurement by the acoustic-wave acquiring apparatus, the release operation may be late only by electric release driving. Therefore, the option of additional manual release to increase the speed of the release operation during the electric release is required in view of safety.

Emergency Compression Release Mechanism

Figure 24:
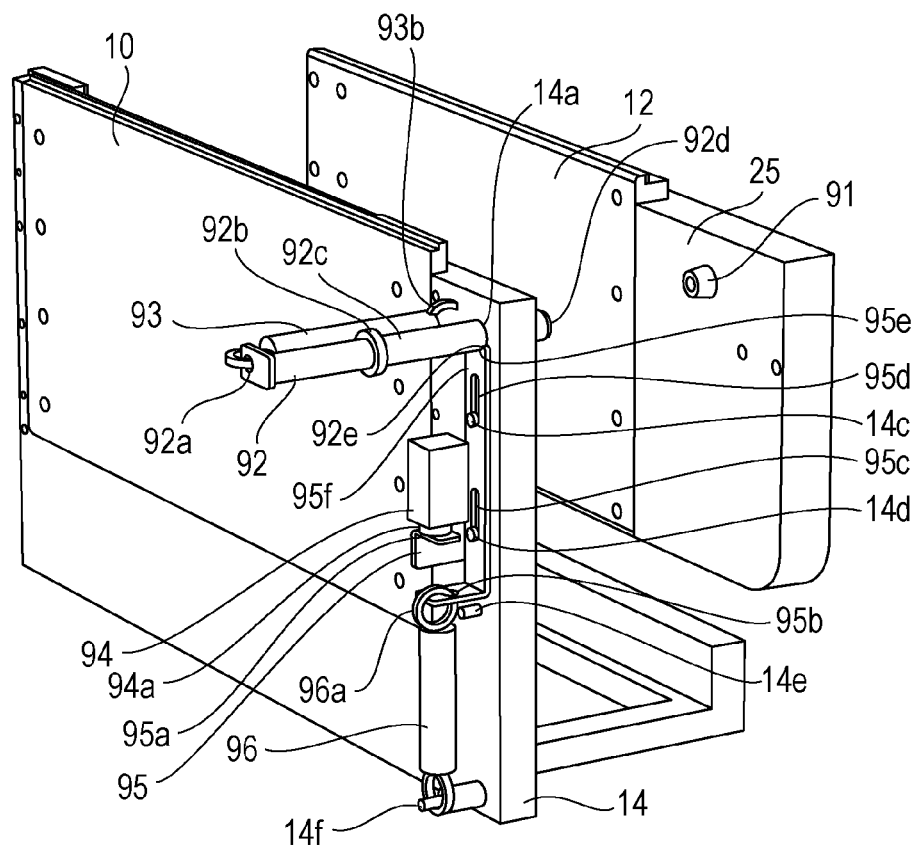
FIG. 24 is an illustration explaining an operation of a compression release mechanism.

Next, an emergency release mechanism for compression is described. FIG. 24 is a perspective view showing an emergency release mechanism according to the embodiment of the present invention. FIGS. 25 to 30 are operation diagrams explaining operations of the emergency release mechanism for compression according to the embodiment of the present invention.

In FIG. 24, reference sign 91 denotes a compression-plate stopper mounted on the compression-plate holder 25. When the movable compression plate 12 is manually or electrically moved in the compression direction, if a breast or a breast phantom 9 is not set, the movable compression plate 12 may contact the compression-plate guide 14 of the fixed compression plate 10. Hence, a rubber stopper may be provided to prevent a finger or the like from being pinched and injured or the compression plate from being damaged.

Reference sign 92 denotes an emergency release lever that forcedly retracts the movable compression plate 12 in the release direction. A fitting portion 92c is slidably fitted to a fitting hole 14a provided in the compression plate guide 14, and a tension spring 93 is hooked at a spring hook portion 92a. The tension spring 93 is stretched between the hole 14a of the compression-plate guide 14 and a spring hook portion 93b. Hence, the emergency release lever 92 is constantly urged in a direction in which the compression-plate holder 25 is released. Also, a stopper portion 92b is provided. When a restraint lever 95 at a cut portion 92e slides and restraint is released, the stopper portion 92b is stopped at a flat portion 95f of the restraint lever 95 or an area around the fitting hole 14a of the compression-plate guide 14.

Reference sign 94 denotes an electromagnetic attraction magnet that is an electromagnet that can attract an attraction surface 95a of the restraint lever 95 against a spring force of a tension spring 96. The electromagnetic attraction magnet 94 is constantly energized when the apparatus is in operation, and continuously attracts the restraint lever 95. If the emergency stop button (not shown) is pressed or an abnormal situation such as a power failure or other error occurs, application of electricity is stopped, so that the restraint lever 95 is released.

Reference sign 95 denotes the restraint lever. The restraint lever 95 is mounted such that positioning pins 14c and 14d provided at the compression-plate guide 14 can vertically slide relative to long holes 95c and 95d. A hook portion 96a of the tension spring 96 is hooked at a spring hook portion 95b. The tension spring 96 is urged between the spring hook portion 95b and a spring hook pin portion 14f of the compression-plate guide 14. When the attraction of the electromagnetic attraction magnet 94 is released, the spring hook portion 95b slides downward by an urging force of the tension spring 96, and stops when contacting a stopper pin 14e.

Figure 25:
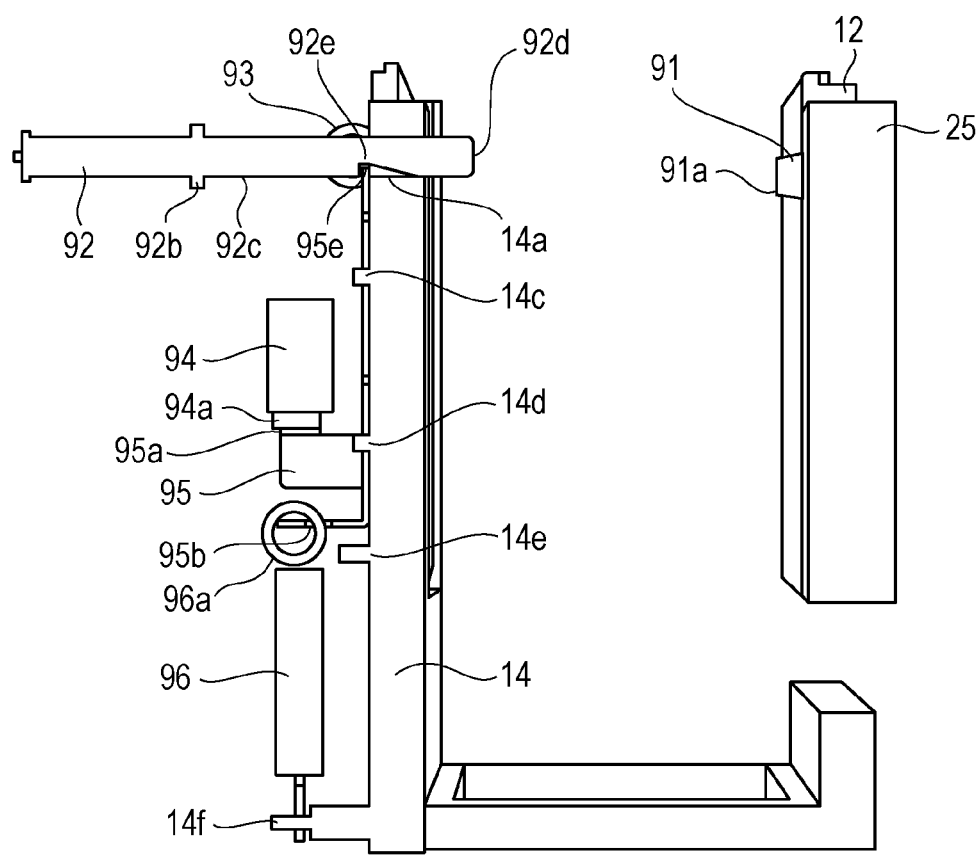
FIG. 25 is an illustration explaining an operation of the compression release mechanism.

An operation of the emergency release mechanism for compression with the above-described configuration is described. FIG. 25 is an illustration of a standby state like FIG. 24. In FIG. 25, a distal end portion 95e of the restraint lever 95 enters the cut portion 92e of the emergency release lever 92 urged rightward by the tension spring 93. Hence, this state is a preparation completed state for emergency release. An attraction portion 94a of the electromagnetic attraction magnet 94 attracts the attraction surface 95a of the restraint lever 95.

Figure 26:
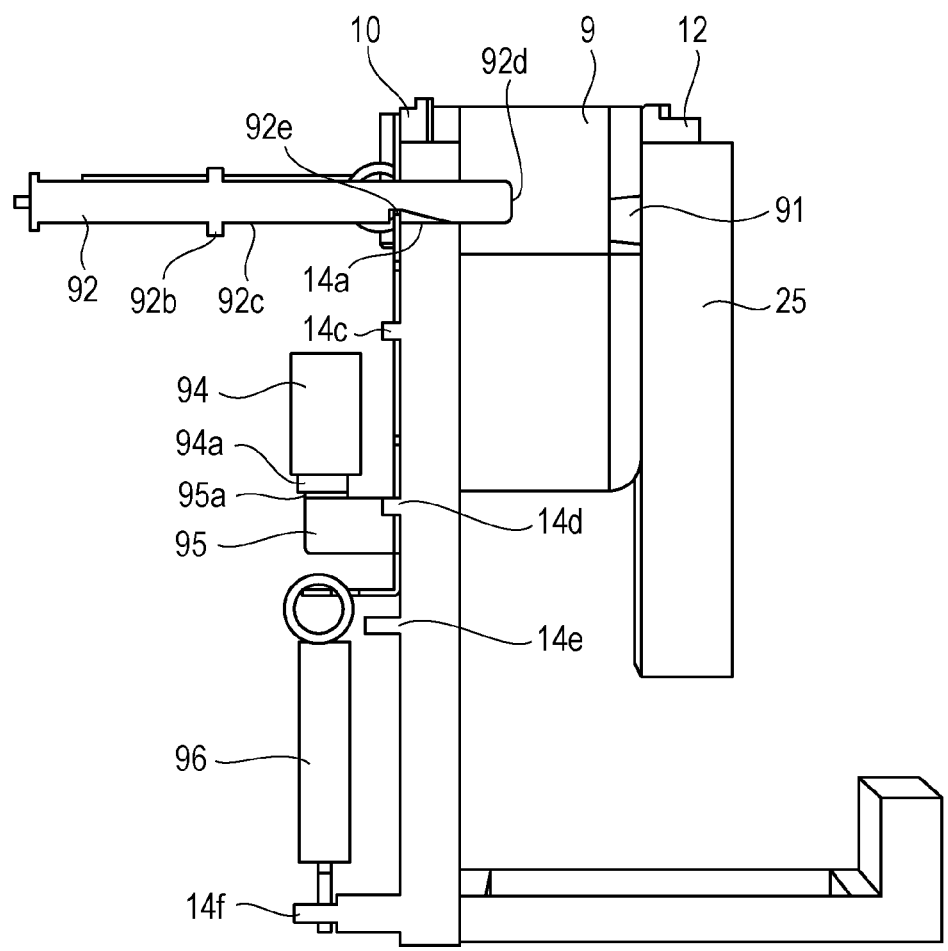
FIG. 26 is an illustration explaining an operation of the compression release mechanism.
Figure 27:
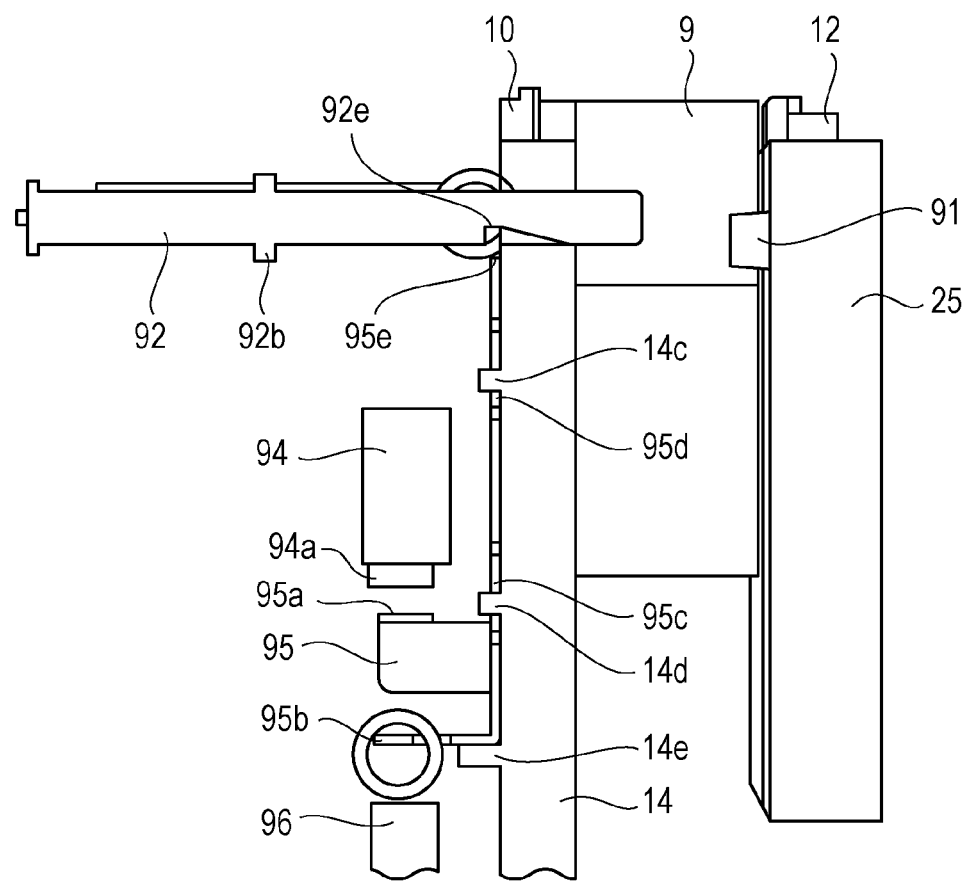
FIG. 27 is an illustration explaining an operation of the compression release mechanism.

FIG. 26 is an illustration showing a state in which the breast phantom 9 is compressed. The emergency release mechanism holds the preparation completed state. FIG. 27 illustrates a state immediately after the emergency release mechanism starts an operation because the emergency stop button (not shown) is depressed or an abnormal situation such as a power failure or other error occurs when the breast or the breast phantom is compressed. First, application of electricity to the electromagnetic attraction magnet 94 is stopped. The restraint lever 95 moves downward by the tension spring 96. Then, the spring hook portion 95b contacts the stopper pin 14e and is stopped. In this state, since the emergency release lever 92 is not moved yet, emergency release for compression is not executed.

Figure 28:
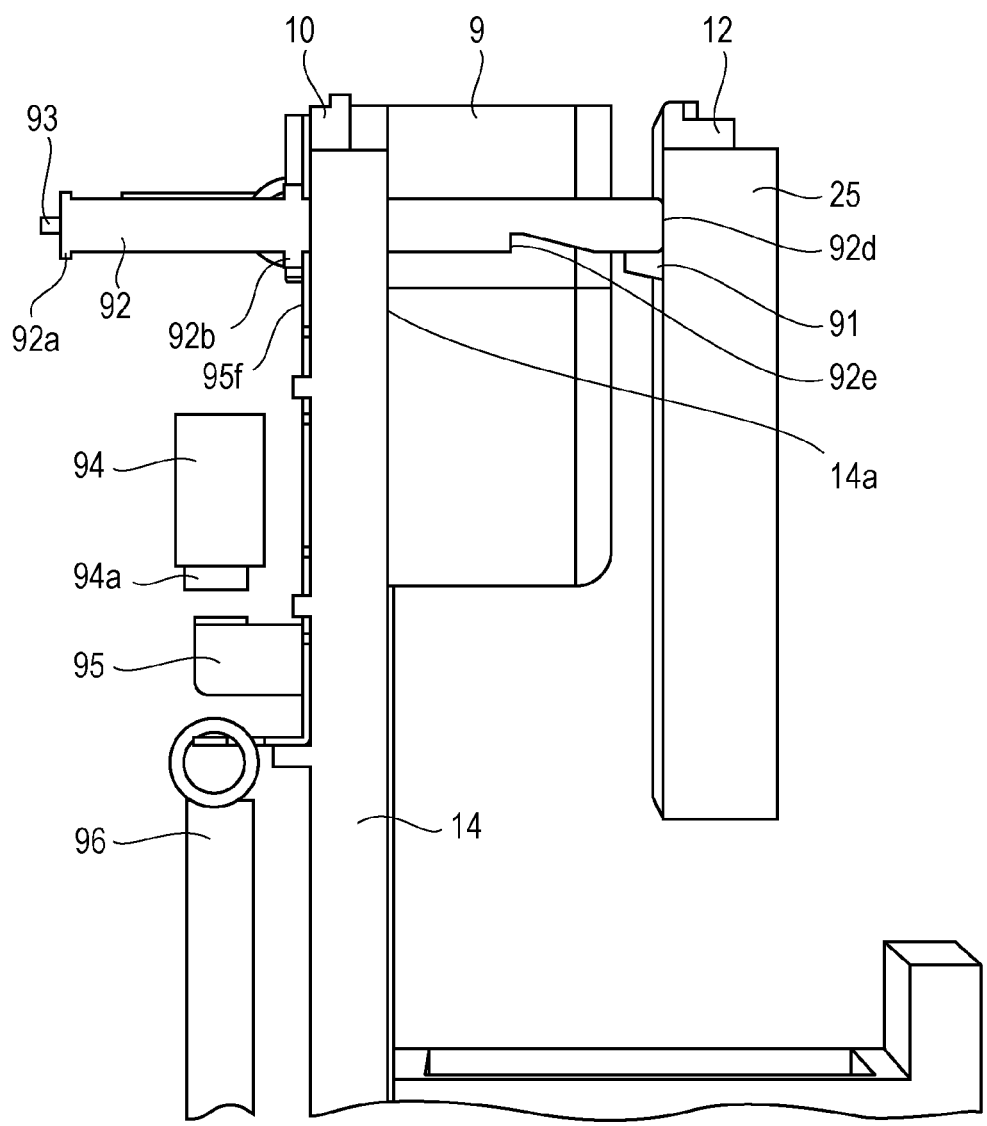
FIG. 28 is an illustration explaining an operation of the compression release mechanism.

FIG. 28 is an illustration showing a state next to the state in FIG. 27. First, the emergency release lever 92 moves rightward along the fitting hole 14a by the tension spring 93. Then, a distal end portion 92d of the emergency release lever 92 presses the compression-plate holder 25, and hence a large gap is made between the breast phantom and the movable compression plate 12. The retraction amount of the movable compression plate 12 is determined such that the stopper portion 92b of the emergency release lever 92 is stopped at the flat portion 95f of the restraint lever 95 or the area around the fitting hole 14a of the compression-plate guide 14. In FIG. 28, the stopper portion 92b is stopped at the flat portion 95f of the restraint lever 95.

In FIG. 28, the gap is widened by the emergency release lever 92 by a width sufficient for removing the breast phantom 9. However, the configuration is not limited to the embodiment. When the emergency release lever 92 performs the release, as shown in FIG. 25, the movable compression plate 12 may be released to a full-open state that is an initial position of the movable compression plate 12. Also, since the strong tension spring 93 causes the emergency release lever 92 to rapidly contact the compression-plate holder 25 for the emergency release, a large sound may be generated. Hence, a sound absorber like a rubber sheet may be provided at the distal end portion 92d of the emergency release lever 92. Alternatively, a rubber sheet may be bonded to a surface of the compression-plate holder that contacts the emergency release lever 92. Accordingly, anxiety of the subject can be eliminated.

If the movable compression plate 12 is driven by the electric drive motor 70 or is manually driven by the manual compression handle 4 in the one-way latch state while the brake 55 with the one-way mechanism is activated, even though the emergency release lever 92 rapidly contacts the compression-plate holder 25 by the strong tension spring 93, the emergency release cannot be carried out. If the emergency stop button (not shown) is pressed or an abnormal situation such as a power failure or other error occurs, application of electricity to the brake 55 with the one-way mechanism is stopped, and application of electricity to the clutch 85 is also stopped. Accordingly, the movable compression plate 12 or the compression-plate holder can be retracted by a small force.

Figure 29:
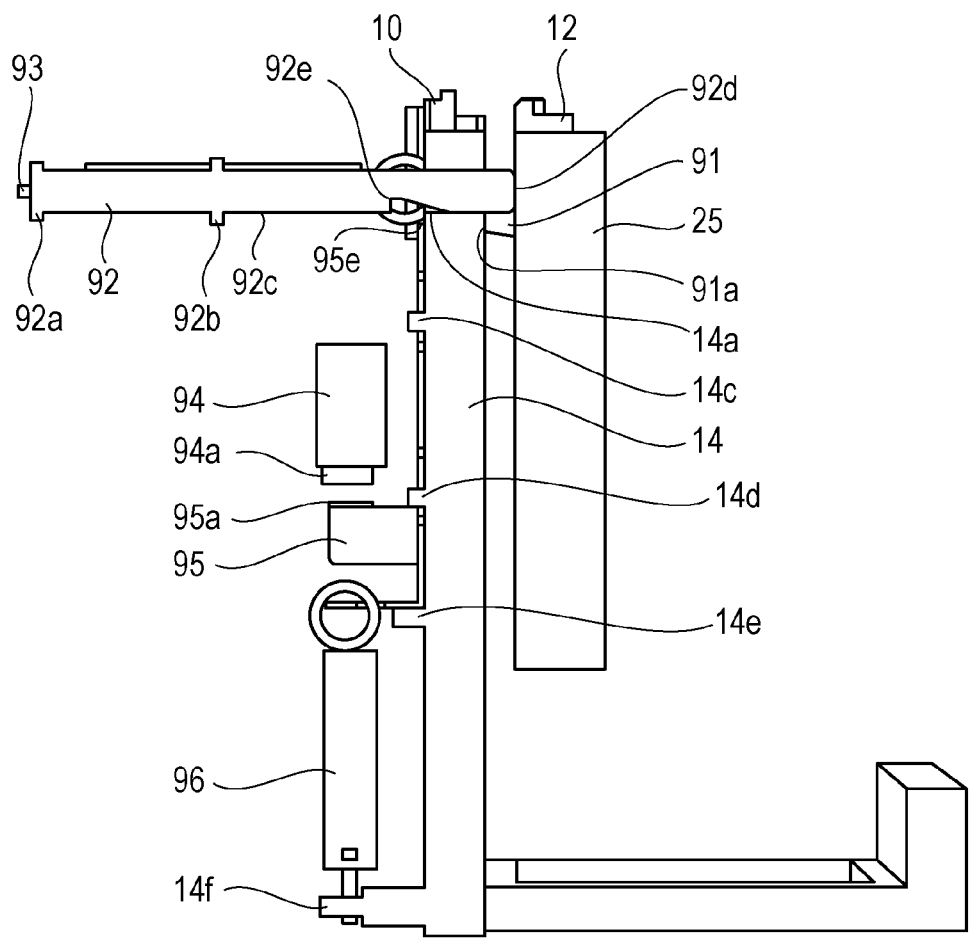
FIG. 29 is an illustration explaining an operation of the compression release mechanism.

As shown in FIG. 28, if the emergency release mechanism is used once, in a case in which a similar situation occurs, the emergency release mechanism may no longer work in the state shown in FIG. 28. Hence, a reset operation of the emergency release mechanism is illustrated in FIG. 29. In FIG. 29, the operation starts from a state in which the breast, the breast phantom, or the like, is removed by the compression release operation after the emergency stop.

In FIG. 29, the operation starts from a state in which a trouble of the apparatus is eliminated, power is supplied again, and the apparatus is in a normal state. First, through system check of the apparatus, it is found that the compression-plate holder is forcedly retracted by the emergency release. Hence, the reset operation is started. First, the clutch is energized so that the electric drive motor 70 is activated and the movable compression plate 12 is driven in the compression direction. Since the potentiometer 61 is provided at the movable compression plate 12, the position of the movable compression plate 12 is immediately determined. Electric driving is started from that position, and electric compression is performed without stopping until a distal end portion 91a of the compression-plate stopper 91 in FIG. 29 contacts the compression-plate guide.

An electric compression driving force at this time is provided up to a compression force of about 70 N under the control of the torque limiter 80. In contrast, the emergency release operation can be performed by about 50 N because an urging force is eliminated. The tension spring 93 can be properly electrically driven although the torque limiter 80 is provided. FIG. 29 is a state in which the reset operation is completed by the electric compression driving. The compression by electric driving is stopped when the compression-plate holder 25 presses the distal end portion 92d of the emergency release lever 92 leftward and the compression-plate stopper 91 contacts the compression-plate guide 14.

Figure 30:
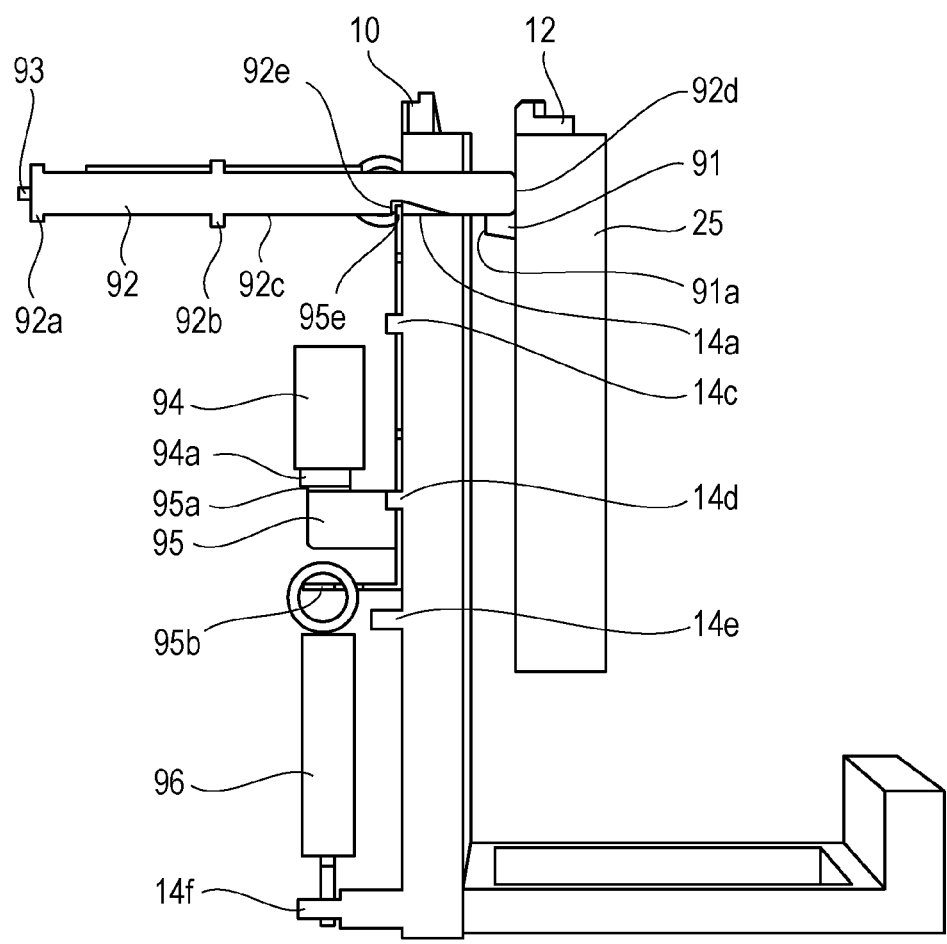
FIG. 30 is an illustration explaining an operation of the compression release mechanism.

In the state in FIG. 29, when the electromagnetic attraction magnet 94 is energized and the restraint lever 95 is attracted, the distal end portion 95e of the restraint lever 95 enters the cut portion 92e of the emergency release lever 92. Hence, the emergency release lever 92 can be brought into the preparation completed state. FIG. 30 illustrates a state in which the electromagnetic attraction magnet 94 is energized and the restraint lever 95 is continuously attracted. FIG. 30 illustrates a state in which reverse driving of the electric drive motor 70 is performed, the compression-plate holder 25 is slightly moved toward the release position, and the emergency release lever 92 is brought into the preparation completed state by the restraint lever 95. From the state in FIG. 30, the electric drive motor 70 is driven in the release direction. Application of electricity is stopped when the movable compression plate 12 becomes full open, and the reset operation of the emergency release mechanism is completed.

Monitor Camera and Illumination Device

Figure 31:
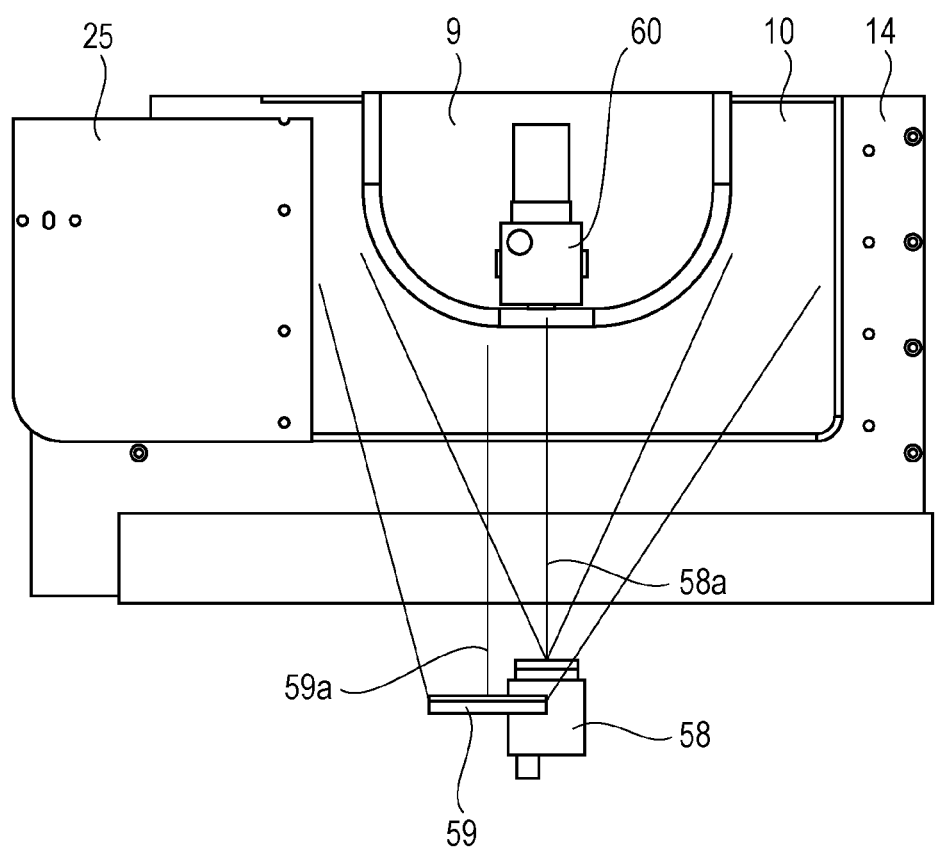
FIG. 31 is an arrangement diagram of a monitor camera and an illumination device.
Figure 32:
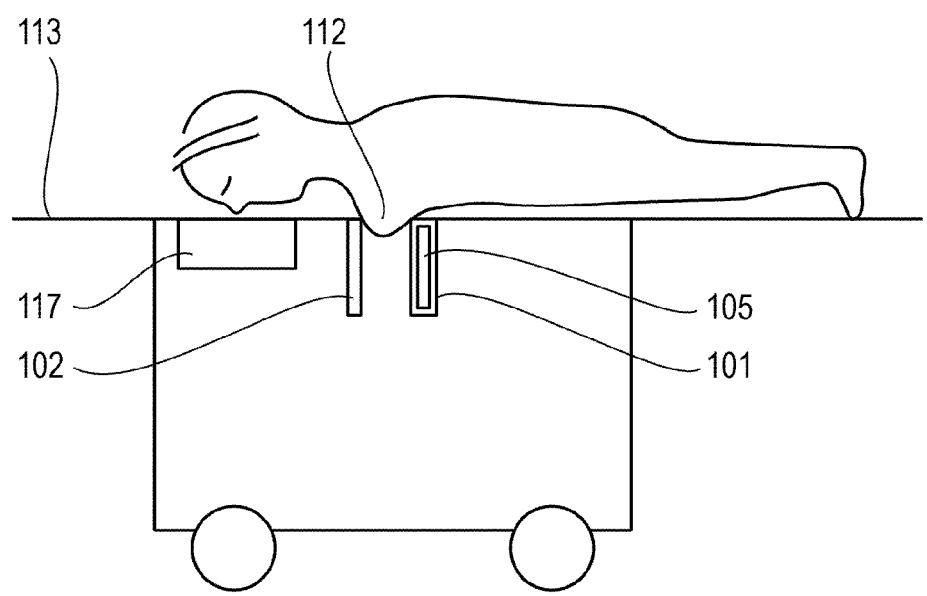
FIG. 32 is a schematic illustration of an X-ray mammography apparatus of related art.

Next, a monitor camera and an illumination device that assist compression according to the embodiment of the present invention are described. FIGS. 12 and 31 are illustrations showing features of the monitor cameras 58 and 60, and the LED illumination device 59. In FIGS. 12 and 31, reference sign 58 denotes the monitor camera for observation from directly below the breast during compression. The monitor camera 58 is arranged at a position near the fixed compression plate 10. As shown in FIG. 31, the position of the monitor camera 58 is substantially at the center of the fixed compression plate.

The monitor camera 58 is a camera for mainly viewing an angle between the subject and the compression plate during MLO measurement. The inventor of the present invention found that there is an inclination angle of the subject with respect to the compression plate at which it is difficult to perform compression in the MLO direction, in a plane parallel to the surface of the bed, through an experiment. Then, the inventor ensured that the compression can be properly performed by aligning the breast with an angle defined by a line formed of a connection position of the breast with a breast muscle at the shoulder side and a line formed of a connection position of the breast with an abdominal muscle at the abdominal portion side. However, the angle (the angle defined by the line formed of the connection position of the breast with the breast muscle at the shoulder side and the line formed of the connection position of the breast with the abdominal muscle at the abdominal portion side) varies among individuals. The angle cannot be determined in an erect position. Thus, according to the embodiment of the present invention, the monitor camera 58 that captures an image of a breast is provided at a position opposite to the breast insertion hole.

With the monitor camera 58, a state of a shape of the breast can be observed from the lower side (side opposite to the breast insertion hole) while the base plate 13 slides. In the state in which the fixed compression plate contacts the breast, if the shape of a distal end portion of the breast viewed from the lower side is substantially parallel to the movable compression plate, it is determined that compression can be properly performed, and hence the movable compression plate is moved. In the state in which the fixed compression plate contacts the breast, if the shape of the distal end portion of the breast viewed from the lower side is inclined with respect to the movable compression plate, it is determined that compression cannot be properly performed. In this case, a relative angle between the subject and the compression plate can be changed. By observing the state of the breast shape of the subject from the lower side during measurement in the MLO direction, the number of times that compression is unnecessarily repeated is reduced and pain of the subject during compression is reduced.

Also, in a case of an apparatus that a manipulation is performed from a lateral side of the subject portion like the acoustic-wave acquiring apparatus according to the embodiment of the present invention, the monitor camera 60 for observation through the compression plate can be provided. Since the monitor camera 60 observes the breast, the monitor camera 60 assists the manipulation when the compressed state of the breast cannot be sufficiently determined from the manipulation side. Accordingly, the number of failures of compression is markedly reduced. The monitor camera 60 may be provided at either one or both of the movable compression plate and the fixed compression plate. If the monitor camera 60 is provided at the fixed compression plate, the positional relationship between the camera and the compression plate can be constantly fixed. If the positional relationship between the camera and the compression plate is fixed, the relationship between an actual size of the breast and an apparent size of the breast displayed on a monitor (display device) is constantly fixed. In contrast, if the camera is provided at the movable compression plate, the positional relationship between the camera and the compression plate has to be calculated and a scale of an image displayed on the monitor has to be changed. However, since the probe etc. is not arranged at the movable compression plate, the apparatus structure can be simple.

Also, according to the embodiment of the present invention, the LED illumination device 59 configured to irradiate the subject portion from the lower side opposite to the breast insertion hole is provided. The LED illumination device 59 provides illumination that allows the monitor cameras 58 and 60 to easily perform image-capturing, and the illumination is not obstructed by a hand during a manipulation. Hence, the captured image of the breast can be easily viewed on the monitor. Also, the illumination position of the LED illumination device 59 is not located at the center of the fixed compression plate 10 unlike the monitor camera 58, but is shifted to the left side with respect to the center (a side opposite to the manipulation opening). As shown in FIGS. 4 and 5, the side opposite to the manipulation opening is the foot side of the subject. That is, in FIG. 31, the left side of any of the left and right breasts is located at the foot side during compression in the MLO direction. This is because, during compression of the breast in the MLO direction, the nipple of the breast is not arranged at the center unlike the position during compression in the CC direction, but is shifted to the foot side.

Hence, with regard to the monitor camera 58, a center axis 59a of the LED illumination device 59 is shifted to the left side (the side opposite to the manipulation opening) with respect to a center axis 58a of the monitor camera 58, so that a shade hardly appears in the illumination. In any embodiment of the present invention, the illumination device does not have to be a LED, and may be an incandescent lamp, a fluorescent lamp, or the like.

Operation of Acoustic-wave Acquiring Apparatus

Figure 22A:
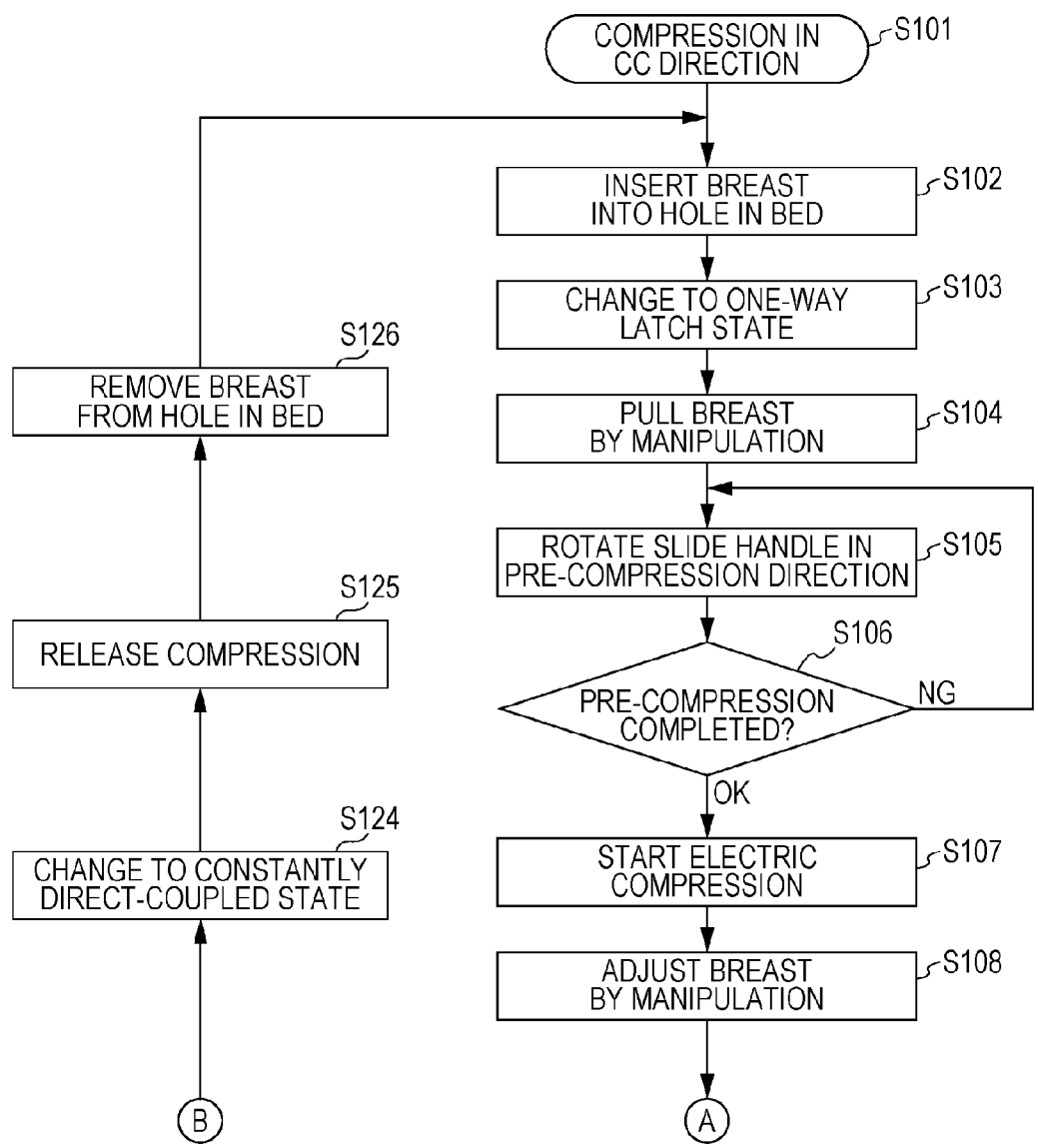
FIGS. 22A and 22B illustrate a flowchart showing a compression sequence according to an embodiment of the present invention.
Figure 22B:
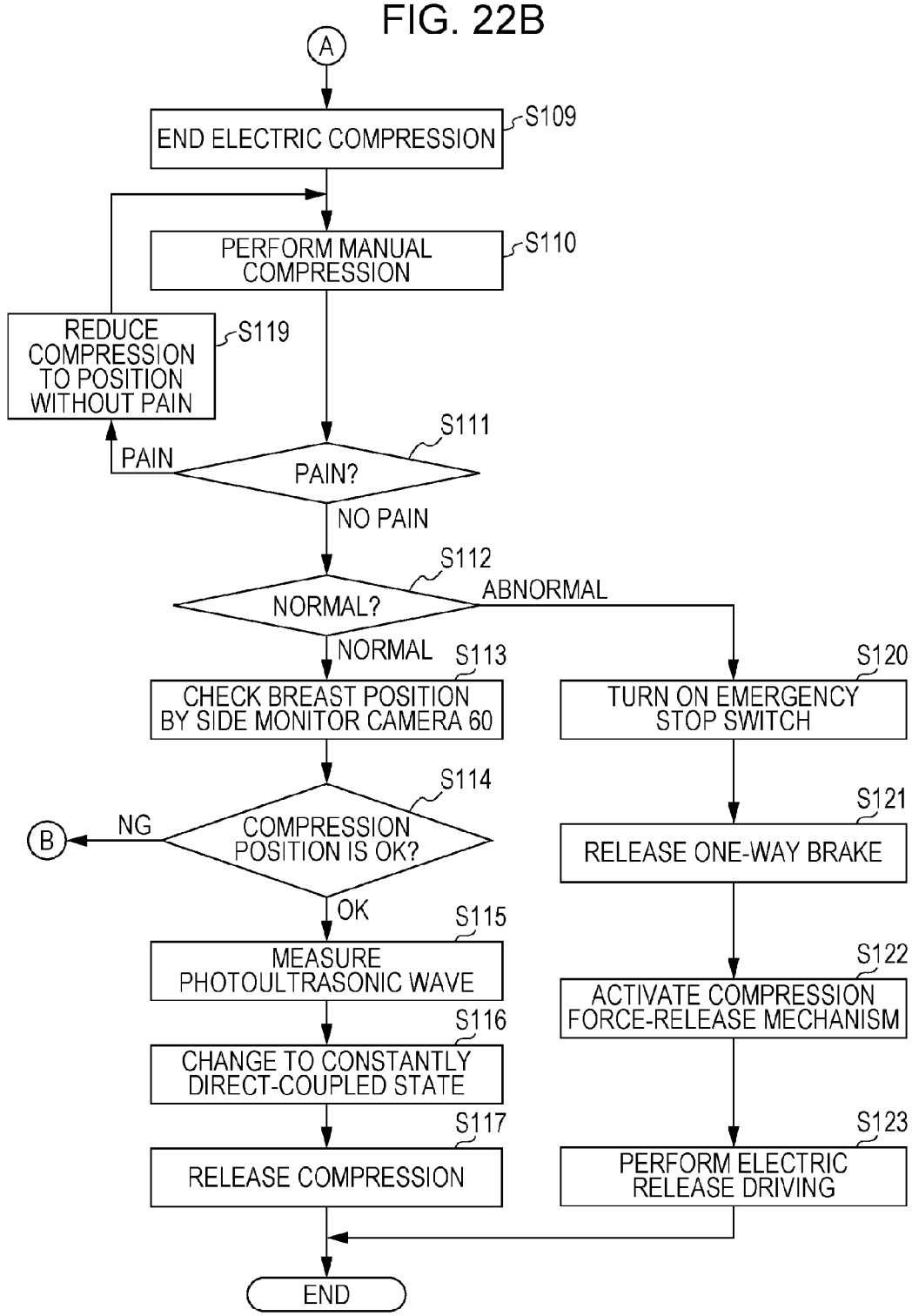

Next, an operation of the acoustic-wave acquiring apparatus is described as an example of a measurement apparatus according to the embodiment of the present invention. FIGS. 22A, 22B, 23A, and 23B are flowcharts showing measurement sequences of the acoustic-wave acquiring apparatus. FIGS. 22A and 22B illustrate measurement during compression in the CC direction.

First, the sequence starts from step S101. In step S102, the subject takes the prone position on the bed, and inserts a breast to be measured into the hole 1a of the bed 1. In step S103, the state change switch 5 changes the state of the compression mechanism to the one-way latch state.

In step S104, when the breast of the subject is sufficiently pulled toward the compression measurement unit 2 by a manipulation, the breast is arranged to sufficiently extend along the fixed compression plate 10 through the manipulation, and the sequence goes to step S105. In step S105, the slide handle 3 is rotated, so that the compression measurement unit 2 slides relative to the bed 1. This sliding provides pre-compression on the breast of the subject from a Cb direction when the breast is at the C position in FIG. 3. That is, when the subject takes the position as shown in FIG. 6, the fixed compression plate 10 is pressed to the breast from the foot side. Accordingly, the under-breast of the breast is fixed, and pre-compression corresponding to one-third to half of full compression is completed.

When the slide handle 3 is rotated counterclockwise in FIG. 14, since the gear 67 is fixed to the shaft of the slide handle 3, the gear 67 rotates counterclockwise similarly, and the rotation is transmitted from the reduction gear 68 to the gear 69. Since the slide rack gear 65 fixed to the base plate 13 meshes with the gear 69, the counterclockwise rotation of the gear 69 causes the slide rack gear 65 to move from the foot side to the head side together with the base plate 13 (step S106). When the pre-compression is completed, the sequence goes to step S107, in which the pedal 6b is depressed to start electric compression. Then, the movable compression plate

12 gradually moves in the compression direction. In step S108, the compressed state of the breast is adjusted by a manipulation.

In step S109, the pedal 6*b* is released to end the electric compression while the hand for the manipulation is removed from the breast. In step S110, the manual compression handle 4 is rotated counterclockwise for manual compression. This manual compression handle 4 is carefully operated while the operator asks the subject whether the subject feels pain or not in step S111. If the subject feels pain, the sequence goes to step S119, in which the manual compression handle 4 is operated clockwise in the release direction of compression, and removes the pain. Then, the sequence goes back to step S110 in which compression is continued from the state without pain.

If an abnormal situation occurs in step S112, the sequence immediately goes to step S120, in which the emergency stop switch (not shown) is turned ON. Then, the system recognizes the abnormal situation, automatically performs steps S121 to S123, that is, the system releases the one-way break at step S121 and activates a forced release of the compression at step S122, so that the compression is automatically released in step S123 by performing electric release driving. Thus, the measurement is stopped. If the abnormal situation does not occur in step S112, an image of the monitor camera 60 that captures the image of the breast from the head side of the movable compression plate 12 is observed through a monitor (not shown) and the compressed state of the breast is checked in step S113. When the monitor camera 60 captures the image of the breast from the head side of the movable compression plate 12, since the LED illumination device 59 provided directly below the fixed compression plate 10 illuminates the breast, the breast can be entirely illuminated.

In step S114, it is judged whether the compression position is OK (proper) or NG (not proper), and if OK, the sequence goes to step S115, in which a photoultrasonic wave is measured by a predetermined procedure. When the measurement of the photoacoustic wave is ended, to release the breast, the state change switch 5 changes the state to the constantly direct-coupled state in step S116. Then, the brake 55 with the one-way mechanism is no longer energized, and release restriction of the movable compression plate 12 is released (release compression). Accordingly, the movable compression plate 12 is slightly retracted by an elastic force of the breast, and the pain of the breast of the subject is reduced. In step S117 addition, the manual compression handle 4 can be rotated clockwise to retract the movable compression plate 12.

Also, the system can recognize that the state change switch 5 changes the state to the constantly direct-coupled state in step S116. When the measurement is ended, the electric drive motor can be rotated clockwise in step S117, and the compression of the movable compression plate 12 can be forcedly released.

In contrast, if the compression position of the breast is NG (not good) in step S114, for example, if the breast is not sufficiently pulled, the measurement cannot be performed. Hence, the sequence goes to step S124, in which the state change switch 5 changes the state to the constantly direct-coupled state, the manual compression handle 4 is rotated clockwise to release the compression in step S125, the breast of the subject is removed once in step S126, and the sequence is performed again from step S102.

Figure 23A:
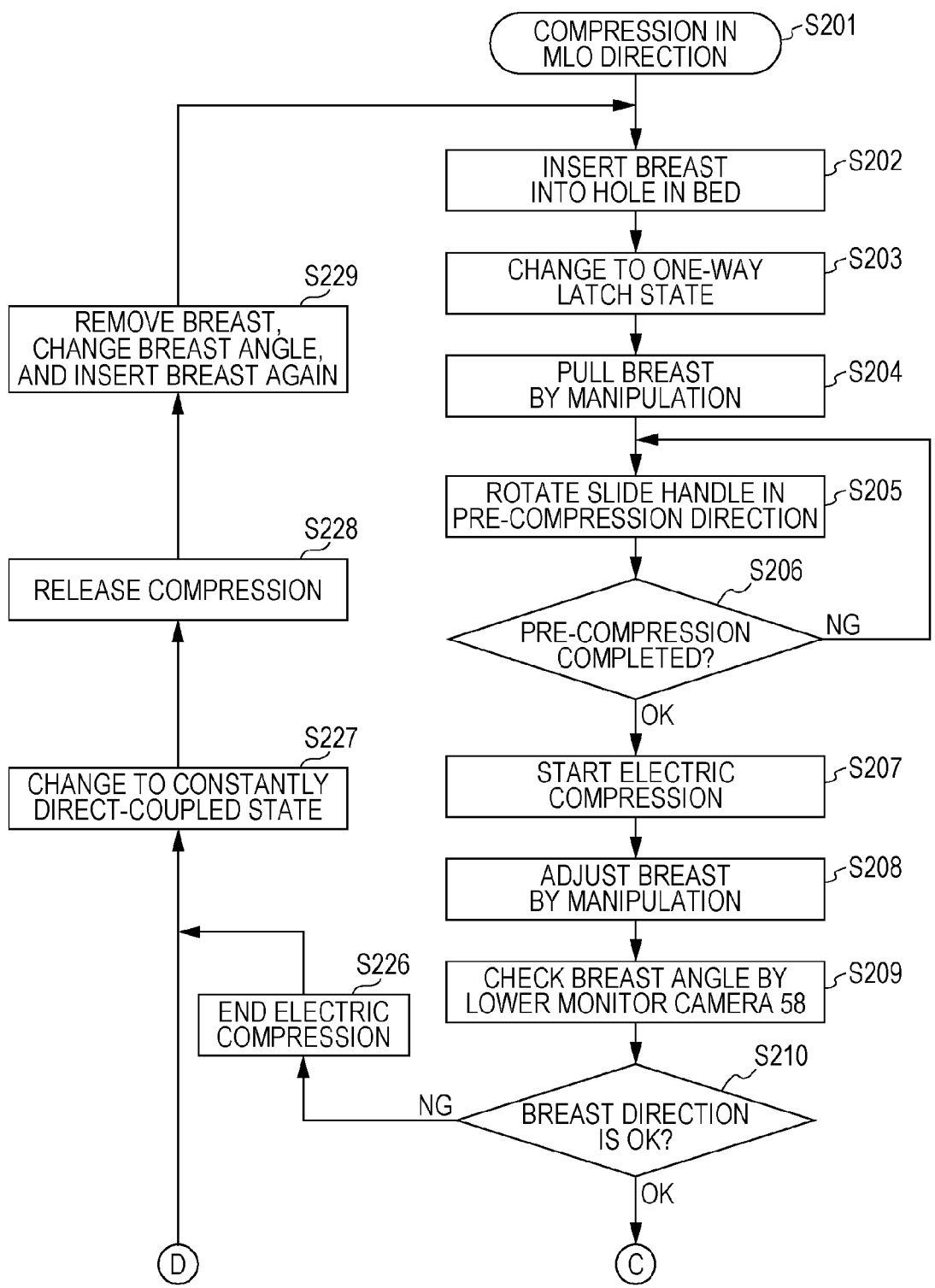

FIGS. 23A and 23B illustrate measurement during compression in the MLO direction. First, the sequence starts from step S201. In step S202, the subject takes the prone position on the bed, and inserts a breast to be measured into the hole 1*a* of the bed 1. When the subject takes the prone position, the angle in the MLO direction has to be instructed unlike the measurement in the CC direction. In step S203, the state change switch 5 changes the state of the compression mechanism to the one-way latch state.

In step S204, when the breast of the subject is sufficiently pulled toward the compression measurement unit 2 by a manipulation, the breast is arranged to sufficiently extend along the fixed compression plate 10 through the manipulation, and the sequence goes to step S205. In step S205, the slide handle 3 is rotated, so that the compression measurement unit 2 slides relative to the bed 1. In case of the right breast, the subject takes the position in FIG. 4, and this sliding provides pre-compression on the breast from the Ab direction at the A position in FIG. 3. In case of the left breast, the subject takes the position in FIG. 5, and this sliding provides pre-compression on the breast from the Bb direction at the B position in FIG. 3.

The pre-compression is similar to that in the CC direction. When the slide handle 3 is rotated counterclockwise in FIG. 14, since the gear 67 is fixed to the shaft of the slide handle 3, the gear 67 rotates counterclockwise similarly, and the rotation is transmitted from the reduction gear 68 to the gear 69. Since the slide rack gear 65 fixed to the base plate 13 meshes with the gear 69, the counterclockwise rotation of the gear 69 causes the slide rack gear 65 to move from the foot side to the head side together with the base plate 13 (step S206). When the pre-compression is completed, the sequence goes to step S207, in which the pedal 6*b* is depressed to start electric compression. Then, the movable compression plate 12 gradually moves in the compression direction. The compressed state of the breast is adjusted by a manipulation in step S208.

In step S209, by using the monitor cameras 58 and 60 provided directly below the compression mechanism and by providing illumination with the LED illumination device 59, the compressed state of the breast is viewed through the monitor (not shown). In step S210, in particular, the monitor camera 58 directly below the compression plate checks whether the angles Ab and Bb in the MLO direction of the breast of the subject in FIG. 3 are OK (proper) or NG (not proper). If the angle is NG, the compressed state is insufficient.

In step S210, if the angle in the MLO direction is OK, the sequence goes to step S211, in which the pedal 6*b* is released to end the electric compression. In step S212, the manual compression handle 4 is rotated counterclockwise for manual compression. This manual compression handle 4 is carefully operated while the operator asks the subject whether the subject feels pain or not in step S213. If the subject feels pain, the sequence goes to step S221, in which the manual compression handle 4 is operated clockwise in the release direction of compression, and removes the pain. Then, the sequence goes back to step S212 in which compression is continued from the state without pain. If an abnormal situation occurs in step S214, the sequence immediately goes to step S222, in which the emergency stop switch (not shown) is turned ON. Then, the system recognizes the abnormal situation, automatically performs steps S223 to S225, that is, the system releases the one-way break at step S223 and activates a forced release of the compression at step S224, so that the compression is automatically released in step S225 by performing electric release driving. Thus, the measurement is stopped.

If an abnormal situation does not occur in step S214, measurement is continued, and an image of the monitor camera 60 that captures the image of the breast from the head side with respect to the movable compression plate 12 is observed through the monitor (not shown) and the compressed state of the breast is checked in step S215. When the monitor camera 60 captures the image of the breast from the head side of the movable compression plate 12, since the LED illumination device 59 provided directly below the fixed compression plate 10 illuminates the breast, the breast can be entirely illuminated. If the compression position is OK in step S216, the sequence goes to step S217, in which a photoultrasonic wave is measured by a predetermined procedure.

When the measurement of the photoacoustic wave is ended, to release the breast, the state change switch 5 changes the state to the constantly direct-coupled state in step S218. Then, the brake 55 with the one-way mechanism is no longer energized, and release restriction of the movable compression plate 12 is released. Accordingly, the movable compression plate 12 is slightly retracted by an elastic force of the breast, and the pain of the breast of the subject is reduced. In step S219, the manual compression handle 4 can be easily rotated clockwise to retract the movable compression plate 12.

Also, the system can recognize that the state change switch 5 changes the state to the constantly direct-coupled state in step S218. When the measurement is ended, the electric drive motor can be rotated clockwise in step S219, and the compression of the movable compression plate 12 can be forcedly released.

In contrast, if the compression position of the breast is NG in step S216, for example, if the breast is not sufficiently pulled, the measurement cannot be performed. Hence, the sequence goes to step S227, in which the state change switch 5 changes the state to the constantly direct-coupled state, the manual compression handle 4 is rotated clockwise to release the compression in step S228, the breast of the subject is removed once in step S229, and the sequence is performed again from step S202.

If the angle in the MLO direction is NG in step S210, the compression may not be sufficient. The angle in which the breast is inserted is changed by rotation around the hole 1a of the bed when the subject takes the prone position, and the compression is performed again. The sequence goes to step S226, in which the pedal 6b is released to stop the electric compression. Next, the sequence goes to step S227, in which the state change switch 5 changes the state to the constantly direct-coupled state. Then, in step S228, the manual compression handle 4 is rotated clockwise and the compression is released. In step S229, the breast of the subject is removed once, and in step S202, the sequence is performed again from the beginning.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-265748 filed Nov. 29, 2010, which is hereby incorporated by reference herein in its entirety.

What is claimed is:

1. An apparatus comprising:
   a bed configured to support a subject and having an insertion hole through which a subject portion which is part of the subject is inserted;
   a compression mechanism including two compression plates and configured to hold and compress the subject portion when the subject portion is inserted in an insertion direction through the insertion hole;
   a manipulation opening formed on one side of the compression mechanism and substantially perpendicular to the insertion hole, wherein the manipulation opening is configured to allow an operator to manipulate the subject portion inserted through the insertion hole; and
   a receiving plate disposed on another side of the compression mechanism at a position away from the manipulation opening and within a range of the insertion hole when viewed from the insertion hole in the insertion direction,
   wherein the receiving plate is arranged at a position facing a back surface of the bed, such that the receiving plate is arranged in contact with upper surfaces of the two compression plates and at substantially the same height of the upper surfaces of the compression plates.

2. The apparatus according to claim 1, wherein the receiving plate is configured to support a body part of the subject inserted through the insertion hole other than the subject portion.

3. The apparatus according to claim 1, wherein the subject portion is a human breast, and
   wherein the receiving plate is provided at the back surface of the bed within a region of the insertion hole in the insertion direction of the breast.

4. The apparatus according to claim 1, wherein the receiving plate is made of a material having Young's modulus within a range from 1.00 to 5.00 GPa.

5. The apparatus according to claim 1, wherein the insertion hole is configured to allow a human breast of the subject to protrude therethrough, and
   wherein the receiving plate is configured to prevent a body part of the subject other than the human breast from protruding through the insertion hole.

6. The apparatus according to claim 1, wherein the two compression plates include a fixed compression plate and a movable compression plate substantially parallel to each other.

* * * * *